US011210922B2

(12) United States Patent
Carr et al.

(10) Patent No.: US 11,210,922 B2
(45) Date of Patent: Dec. 28, 2021

(54) ELECTRONIC FALL MONITORING SYSTEM

(71) Applicant: TIDI Products, LLC, Neenah, WI (US)

(72) Inventors: Roy Seizo Carr, Fontana, CA (US); Glen Holt Humphrey, North Hills, CA (US); Drew Deem Coatney, Chicago, IL (US); Himanshu Patel, Rancho Santa Margarita, CA (US); Lisa McHale, Lafayette, CO (US); Brian N. Young, Highland Park, IL (US); Justin K. Thomas, Niles, IL (US)

(73) Assignee: TIDI Products, LLC, Neenah, WI (US)

( * ) Notice: Subject to any disclaimer, the term of this patent is extended or adjusted under 35 U.S.C. 154(b) by 0 days.

(21) Appl. No.: 16/907,603

(22) Filed: Jun. 22, 2020

(65) Prior Publication Data
US 2020/0320843 A1 Oct. 8, 2020

Related U.S. Application Data

(63) Continuation-in-part of application No. 16/423,348, filed on May 28, 2019, now Pat. No. 10,692,346.
(Continued)

(51) Int. Cl.
  *G08B 23/00* (2006.01)
  *G08B 21/04* (2006.01)
  (Continued)

(52) U.S. Cl.
  CPC .......... *G08B 21/0446* (2013.01); *A61B 5/002* (2013.01); *A61B 5/1117* (2013.01);
  (Continued)

(58) Field of Classification Search
  CPC ............ G08B 21/0446; G08B 21/0277; G08B 21/023; G08B 21/043; G01P 13/00;
  (Continued)

(56) References Cited

U.S. PATENT DOCUMENTS 4,907,845 A 3/1990 Wood
5,554,835 A 9/1996 Newham
(Continued)

OTHER PUBLICATIONS

"Sitter Elite Instruction Manual", manual, 2015, 40 pages, Posey Company, Arcadia, California.
(Continued)

*Primary Examiner* — Toan N Pham
(74) *Attorney, Agent, or Firm* — Epiphany Law, LLC

(57) ABSTRACT

The present invention provides an improved electronic fall monitoring system comprising a device having multiple sensor ports for flexibly monitoring various sensors associated with a single patient without requiring repeated connections and disconnections of sensors. With several sensors simultaneously connected at different locations, a processor can execute to ensure that only one sensor, corresponding to one patient, is monitored at any given time, including by triggering an alarm when a second sensor is triggered while a first sensor is in use. Accordingly, the system can provide a "one step transfer" in which a caregiver may simply press hold once to transfer a patient from one sensed area to another. In addition, the caregiver can simply actuate a single input with only a momentary press to allow suspension of monitoring for a shorter duration (hold) or a longer press to allow suspension of monitoring for a longer duration (extended hold).

20 Claims, 18 Drawing Sheets

Related U.S. Application Data

(60) Provisional application No. 62/748,886, filed on Oct. 22, 2018.

(51) Int. Cl.
*G01P 13/00* (2006.01)
*G08B 21/02* (2006.01)
*A61B 5/11* (2006.01)
*A61B 5/00* (2006.01)

(52) U.S. Cl.
CPC .......... *A61B 5/742* (2013.01); *A61B 5/7405* (2013.01); *A61B 5/746* (2013.01); *A61B 5/7465* (2013.01); *G01P 13/00* (2013.01); *G08B 21/023* (2013.01); *G08B 21/0277* (2013.01); *A61B 2560/0214* (2013.01)

(58) Field of Classification Search
CPC ..... A61B 5/1117; A61B 5/002; A61B 5/7405; A61B 5/7465; A61B 5/742; A61B 5/746; A61B 2560/0214; A61B 21/043
See application file for complete search history.

(56) References Cited

U.S. PATENT DOCUMENTS

| | | | |
|---|---|---|---|
| 5,751,214 A | 5/1998 | Cowley et al. | |
| 5,844,488 A | 12/1998 | Musick | |
| 6,078,261 A | 6/2000 | Davsko | |
| 6,111,509 A | 8/2000 | Holmes | |
| 6,166,644 A | 12/2000 | Stroda | |
| 6,441,742 B1 | 8/2002 | Lovely et al. | |
| 6,727,445 B2 | 4/2004 | Cullinan et al. | |
| 6,784,797 B2 | 8/2004 | Smith et al. | |
| 6,847,301 B1 | 1/2005 | Olson | |
| 6,897,781 B2 | 5/2005 | Cooper et al. | |
| 6,987,232 B2 | 1/2006 | Smith et al. | |
| 6,998,986 B2 | 2/2006 | Smith | |
| 7,078,676 B2 | 7/2006 | Smith et al. | |
| 7,079,036 B2 | 7/2006 | Cooper et al. | |
| 7,253,366 B2 | 8/2007 | Bhai | |
| 7,319,400 B2 | 1/2008 | Smith et al. | |
| 7,378,975 B1 | 5/2008 | Smith et al. | |
| 7,557,719 B1 | 7/2009 | Long | |
| 7,568,246 B2 | 8/2009 | Weismiller et al. | |
| 7,570,152 B2 | 8/2009 | Smith et al. | |
| 7,656,299 B2 | 2/2010 | Gentry et al. | |
| 7,666,151 B2 | 2/2010 | Sullivan et al. | |
| 7,746,218 B2 | 6/2010 | Collins, Jr. et al. | |
| 7,883,480 B2 | 2/2011 | Dunlop | |
| 7,916,036 B1 | 3/2011 | Pope et al. | |
| 8,085,154 B2 | 12/2011 | Williams et al. | |
| 8,325,053 B2 | 12/2012 | Flynt et al. | |
| 8,416,084 B2 | 4/2013 | Beltmann et al. | |
| 8,604,917 B2 | 12/2013 | Collins et al. | |
| 8,717,181 B2 | 5/2014 | Tallent et al. | |
| 8,749,391 B2 | 6/2014 | Flinsenberg et al. | |
| 8,752,220 B2 | 6/2014 | Sodeberg et al. | |
| 8,866,620 B2 | 10/2014 | Amir | |
| 8,911,377 B2 | 12/2014 | Al-Ali | |
| 8,933,801 B2 | 1/2015 | Sweeney et al. | |
| 8,990,041 B2 | 3/2015 | Grabiner et al. | |
| 9,013,313 B2 | 4/2015 | Paine | |
| 9,098,993 B2 | 8/2015 | Reed, Jr. | |
| 9,153,114 B2 | 10/2015 | Yi et al. | |
| 9,202,361 B2 | 12/2015 | Rubio Andres et al. | |
| 9,275,533 B2 | 3/2016 | Sullivan et al. | |
| 9,411,934 B2 | 8/2016 | Robinson et al. | |
| 9,466,204 B2 | 10/2016 | Olson | |
| 9,495,855 B2 | 11/2016 | Hanson et al. | |
| 9,558,641 B2 | 1/2017 | Brasch et al. | |
| 9,861,321 B2 | 1/2018 | Collins, Jr. et al. | |
| 9,866,797 B2 | 1/2018 | Clark et al. | |
| 10,043,368 B1 | 8/2018 | Fonzi, III et al. | |
| 10,098,593 B2 | 10/2018 | Collins, Jr. et al. | |
| 2003/0197614 A1* | 10/2003 | Smith | A61B 5/6892 340/573.1 |
| 2007/0040692 A1* | 2/2007 | Smith | A61B 5/1115 340/573.1 |
| 2010/0298742 A1 | 11/2010 | Perlman et al. | |
| 2012/0095722 A1 | 4/2012 | Ten Kate | |
| 2014/0221876 A1 | 8/2014 | Eddy | |
| 2014/0232556 A1 | 8/2014 | Williams | |
| 2015/0226764 A1 | 8/2015 | Ten Kate | |
| 2017/0124844 A1 | 5/2017 | Huster et al. | |
| 2017/0236398 A1 | 8/2017 | Eddy et al. | |
| 2018/0125413 A1 | 5/2018 | Smith, Jr. et al. | |

OTHER PUBLICATIONS

"Fall Management System M200 Fall Monitor", manual, 2016, 44 pages, Stanley Security Solutions, Lincoln, Nebraska.

\* cited by examiner

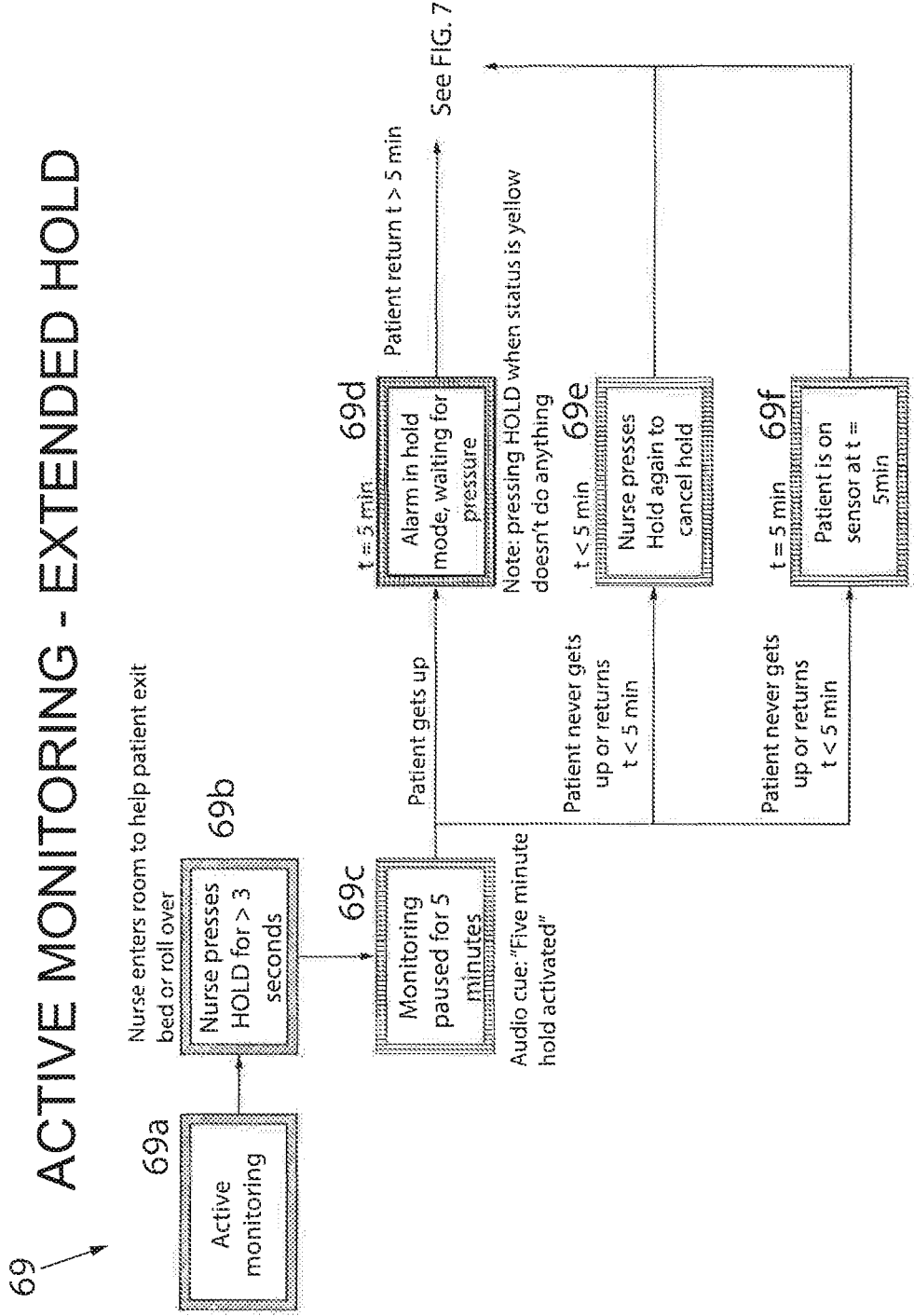

us 11,210,922 B2

ELECTRONIC FALL MONITORING SYSTEM

CROSS-REFERENCE TO RELATED APPLICATIONS

This application claims priority to U.S. patent application Ser. No. 16/423,348, now U.S. Pat. No. 10,692,346, entitled "Electronic Fall Monitoring System," filed on May 28, 2019, which claims priority to U.S. provisional patent application No. 62/748,886, entitled "Electronic Fall Monitoring System," filed Oct. 22, 2018, the contents of each of which are incorporated herein by reference.

FIELD OF THE INVENTION

The present invention relates to the field of patient care, and more particularly, to electronic fail monitoring systems connecting to patient sensors in a patient care setting.

BACKGROUND OF THE INVENTION

Electronic fall monitoring systems are typically used in healthcare facilities to provide an early warning as to when a patient who is at risk for falling is attempting to get up without assistance. Although fall monitoring systems do not themselves prevent falls, they can provide advance notification to others that a patient is moving from the sensor so that assistance can be rendered.

Fall monitoring systems typically include a device connected to a pressure sensitive sensor or mat. When a patient rests on the sensor, which could be placed on a bed or chair, the sensor triggers the device to begin monitoring. When the patient later moves from the sensor, unless the device is suspended or powered down, the device can initiate an alarm. Possible alarms include an audible tone, playback of a recorded statement to return to the sensor and/or a message sent to a nurse call station. While fall monitoring systems are effective for providing early warning when a patient is moving, it is nevertheless desirable to increase their capability, robustness and ease of use where possible.

SUMMARY OF THE INVENTION

The present invention provides an improved electronic fall monitoring system comprising a device having multiple sensor ports for flexibly monitoring various sensors associated with a single patient without requiring repeated connections and disconnections of sensors. With several sensors simultaneously connected at different locations, a processor can execute to ensure that only one sensor, corresponding to one patient, is monitored at any given time, including by triggering an alarm when a second sensor is triggered while a first sensor is in use. Accordingly, in one aspect, the system can provide a "one step transfer" in which a caregiver may simply press hold once to transfer a patient from one sensed area to another, such as from bed to chair. In addition, the caregiver can simply actuate a single input with only a momentary press to allow suspension of monitoring for a shorter duration (hold) or a longer press to allow suspension of monitoring for a longer duration (extended hold).

Sensors can include pads for chairs, beds and toilets, and alarm belts and wearable devices. Sensors can indicate presence or absence of a patient on the sensor, and in some cases, a patient's position, relative patient movement, a patient's movement between zones, and/or rate of patient movement. Also, the system can be configured to latch an alarm, meaning an active alarm continues even if the alarm condition is satisfied and no longer occurring (a patient returning to a sensor), or not latch the alarm, meaning an active alarm stops when the alarm condition is satisfied and no longer occurring (the patient returning to the sensor).

In addition, operation of the device can be simplified with a single multi-color LED illuminating in different colors corresponding to different states of the system. Also, a power switch for turning the device on or off, such as for conserving power, can be placed in a recess of the device so that it is blocked when mounted, thereby avoiding being turned off when it should be monitoring.

Specifically then, one aspect of the present invention can provide an electronic fall monitoring system, including: multiple sensor ports, each sensor port being operable to connect to a patient sensor for detecting an activation indicating a physical presence at the patient sensor and a deactivation indicating a loss of physical presence at the patient sensor; a standby input; and a processor executing a program stored in a non-transient medium, the processor executing the program to: select a mode from among multiple modes, the modes including a monitor mode in which a sensor port connected to a patient sensor is monitored for a deactivation, an alarm mode in which an alarm is active following a deactivation detected in the monitor mode, and a standby mode in which the alarm is inactive, in which the standby mode is selected before an activation is detected at any sensor port, the monitor mode is selected when an activation is detected at a first sensor port, the alarm mode is selected when a deactivation is detected at the first sensor port following the activation, and selection of the standby input causes a temporary transition to the standby mode from either the monitor mode or the alarm mode.

Another aspect of the present invention can provide an electronic fall monitoring system, including: multiple sensor ports, each sensor port being operable to connect to a patient sensor for detecting an activation indicating a physical presence at the patient sensor and a deactivation indicating a loss of physical presence at the patient sensor; a multi-color Light Emitting Diode (LED); and a processor executing a program stored in a non-transient medium, the processor executing the program to: select a mode from among multiple modes, the modes including a monitor mode in which a sensor port connected to a patient sensor is monitored for a deactivation, an alarm mode in which an alarm is active following a deactivation detected in the monitor mode, and a standby mode in which the alarm is inactive, and illuminate the multi-color LED in a given color for indicating a given mode of the plurality of modes.

Another aspect of the present invention can provide an electronic fall monitoring system, including: a housing enclosing electronics including a processor; multiple sensor ports accessible through the housing, each sensor port being operable to connect to a patient sensor for allowing the processor to detect an activation indicating a physical presence at the patient sensor and a deactivation indicating a loss of physical presence at the patient sensor; a power switch accessible through the housing for controlling power to the electronics; and a recess in the housing shaped for mounting the housing to a support mechanism, in which the power switch is disposed in the recess so that the power switch is inaccessible when the housing is mounted to the support mechanism. Another aspect of the present invention can provide an electronic fall monitoring system, including: first and second sensor ports, each sensor port being operable to connect to a patient sensor for detecting an activation indicating a physical presence at a patient sensor and a deactivation indicating a loss of physical presence at a patient sensor; and a processor executing a program stored in a non-transient medium, the processor executing the program to: select a mode from multiple modes, the modes including a monitor mode in which a sensor port connected to a patient sensor is monitored for a deactivation, an alarm mode in which an alarm is active following a deactivation detected in the monitor mode, and a standby mode in which the alarm is held inactive, in which selection of the monitor mode monitors one of the first and second sensor ports for a deactivation of a patient sensor while monitoring the other of the first and second sensor ports for activation of a patient sensor.

Another aspect of the present invention can provide an electronic fall system, including: first and second indicators; multiple sensor ports, each sensor port being operable to connect to a patient sensor for detecting an activation indicating a physical presence at a patient sensor and a deactivation indicating a loss of physical presence at a patient sensor; and a processor executing a program stored in a non-transient medium, the processor executing the program to: select a mode from multiple modes, the modes including a monitor mode in which a sensor port connected to a patient sensor is monitored for a deactivation, an alarm mode in which an alarm is active following a deactivation detected in the monitor mode, and a standby mode in which the alarm is held inactive; activate the first indicator to correspond to the mode selected from the modes; and activate the second indicator to correspond to a power condition.

Another aspect of the present invention can provide an electronic fall system, including: multiple sensor ports, each sensor port being operable to connect to a patient sensor for detecting an activation indicating a physical presence at a patient sensor and a deactivation indicating a loss of physical presence at a patient sensor; and a user selectable input; and a processor executing a program stored in a non-transient medium, the processor executing the program to: select a mode from multiple modes, the modes including a monitor mode in which a sensor port connected to a patient sensor is monitored for a deactivation, an alarm mode in which an alarm is active following a deactivation detected in the monitor mode, and a standby mode in which the alarm is held inactive, in which selection of the user selectable input for a shorter duration causes a transition to the standby mode for a shorter amount of time, and in which selection of the user selectable input for a longer duration causes a transition to the standby mode for a longer amount of time.

These and other objects, advantages and aspects of the invention will become apparent from the following description. The particular objects and advantages described herein can apply to only some embodiments falling within the claims and thus do not define the scope of the invention. In the description, reference is made to the accompanying drawings which form a part hereof, and in which there is shown a preferred embodiment of the invention. Such embodiment does not necessarily represent the full scope of the invention and reference is made, therefore, to the claims herein for interpreting the scope of the invention.

BRIEF DESCRIPTION OF THE DRAWINGS

Preferred exemplary embodiments of the invention are illustrated in the accompanying drawings in which like reference numerals represent like parts throughout, and in which:

FIG. 10B is a flow chart illustrating single sensor monitoring and extended hold with an electronic fall monitoring system in accordance with an aspect of the invention;

DETAILED DESCRIPTION OF THE INVENTION

Referring now to FIGS. 1-4, in accordance with an aspect of the invention, in front, rear and first and second side views, respectively, an electronic fall monitoring system 10 can comprise a device 12 connected to multiple patient sensors (not shown) for providing an early warning as to when a patient who is at risk for filling is attempting to get up without assistance. As shown in the front view of FIG. 1, the device 12 can include a microphone 14 (labeled "MIC"), a speaker 16, a larger indicator, typically a multi-color Light Emitting Diode (LED) 18 (labeled "STATUS"), and a smaller battery level indicator, typically a battery level indicator LED 20. The microphone 14 can be used to record a statement which could be played back through the speaker 16 ("audio cue" or "audible cue"), such as a recorded statement played to a patient to return to the sensor when alarming. The device 12 can ensure a good statement or input is recorded (non-accidental) for the audio cue by requiring all recordings be of at least a minimum duration, such as 3 seconds, to properly register the recording as a recorded statement for audio cues. The speaker 16 can be used to sound an alarm, such as an audible tone and/or playback of the recorded statement, and/or can be used to play audible cues, such as instructions for setting up the fall monitoring system 10, instructions for resolving an alarm condition, indication of connection or disconnection of a patient sensor or nurse call, and the like. The multi-color LED 18 can indicate by color various modes of operation of the fall monitoring system 10, such as illuminating a relatively slower (slow) flashing green to indicate a "monitor mode" in which a sensor port connected to a patient sensor is being monitored for a deactivation, illuminating a relatively faster (fast or rapid) flashing red to indicate an "alarm mode" in which an alarm is active following a deactivation detected in the monitor mode and/or illuminating a relatively slower (slow) flashing yellow to indicate a "standby mode" in which the alarm is inactive. The battery level indicator LED 20 can indicate a status or charge of batteries powering the device 12, such as when disconnected from a wired power source, such as by flashing red when the battery is low (for example, below 20% charge, or a determination of a predetermined number of days of charge remaining, such as less than three days of charge remaining). This essentially simplifies readability of the device.

Figure 1:
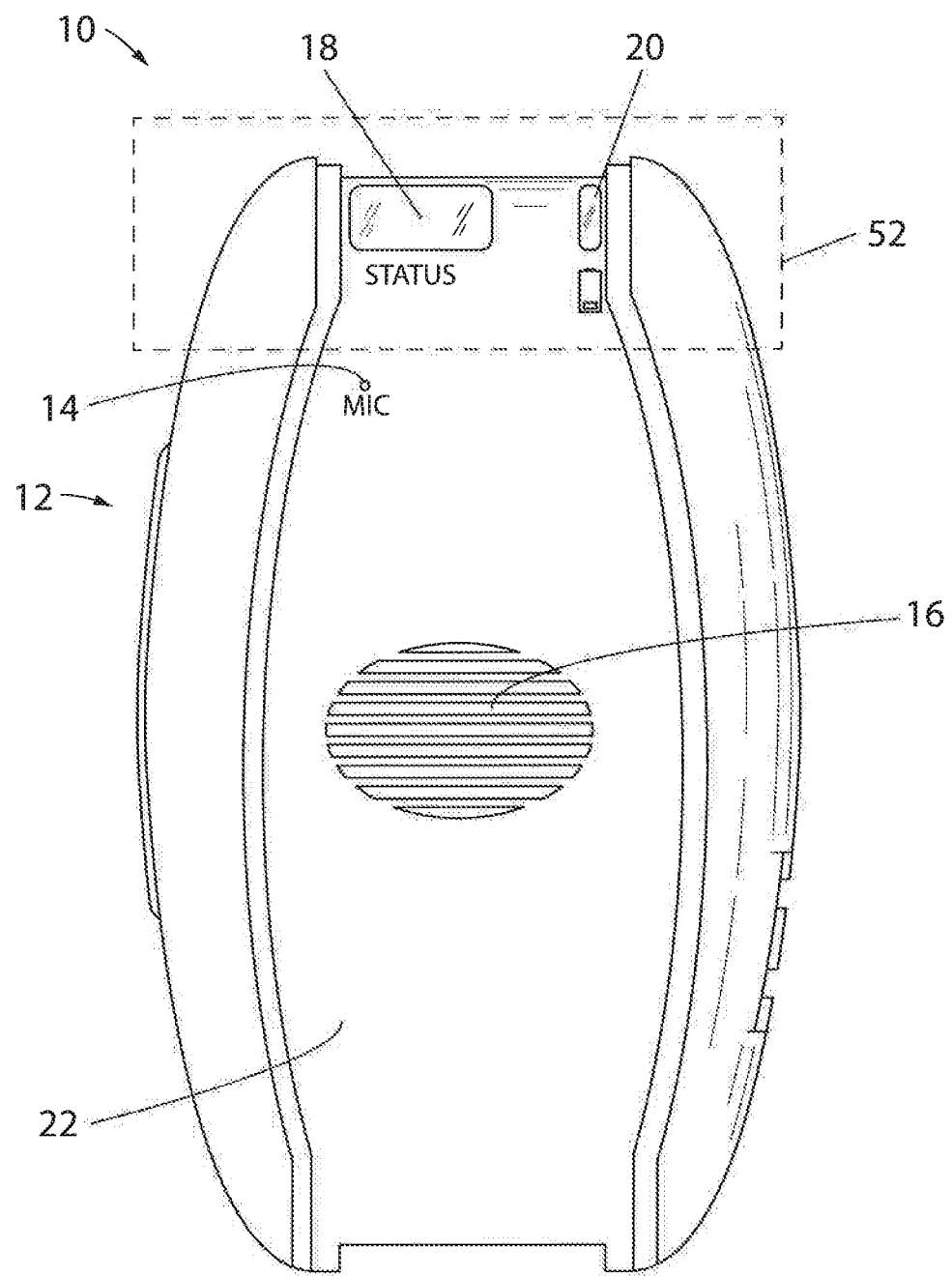
FIG. 1 is a front view of an electronic fall monitoring system in accordance with an aspect of the invention.
Figure 2:
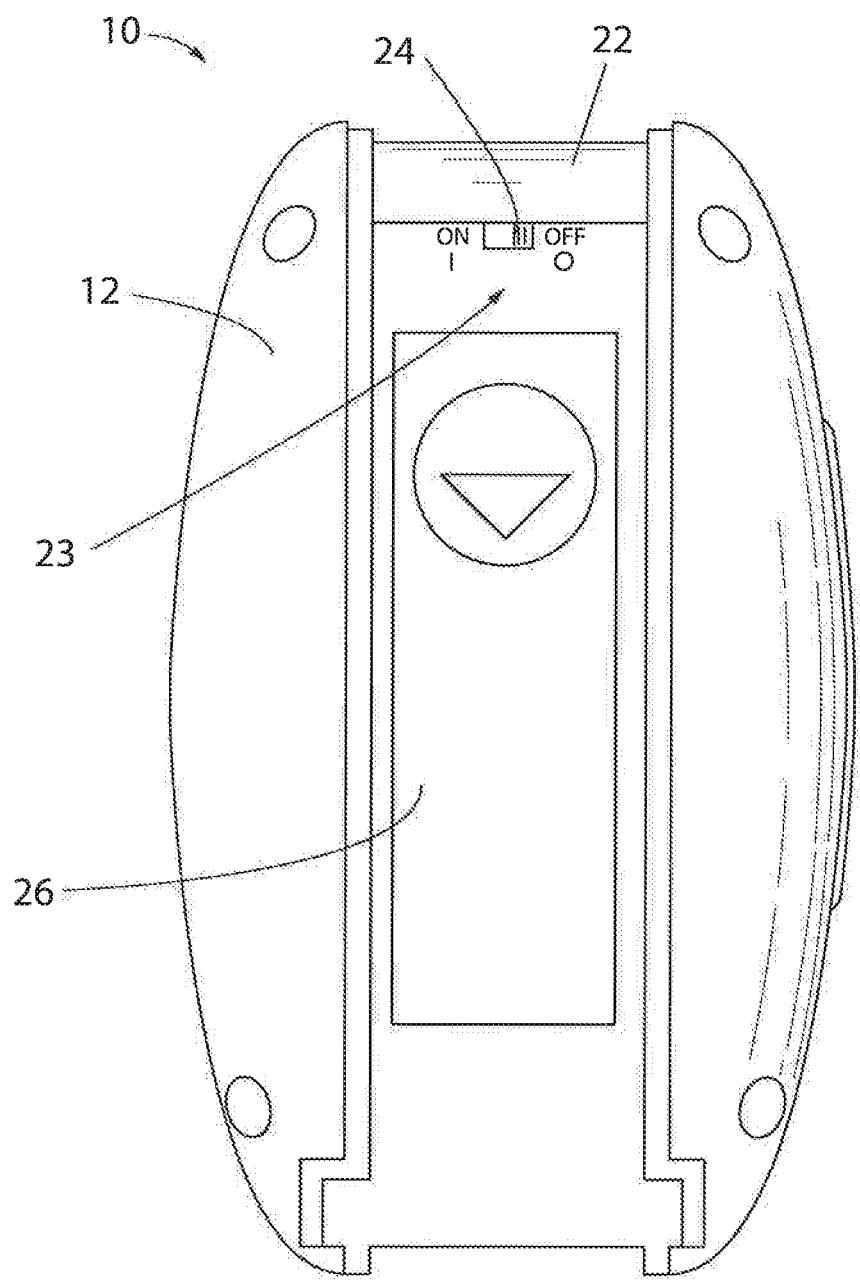
FIG. 2 is a rear view of the electronic fall monitoring system of FIG. 1.

As shown in the rear view of FIG. 2, a back portion of an external housing 22 or enclosure of the device 12 can include a recess 23 for mounting the device 12 to a support mechanism. The support mechanism could be, for example, a bracket, clip, bar or other arrangement held to a structure, such as a wall or chair. A power switch 24 can be accessible through the housing 22 for controlling power to electronics of the device 12, such as a processor or controller as described herein, for turning the device 12 on or off. In one aspect, the electronics of the device 12 could be implemented on four-layer circuit board with a plurality of diodes providing electrostatic discharge (ESD) protection with respect to the various ports as described herein. The power switch 24 can be configured to allow actuation by hand, such as a finger sliding a manual electric switch, without requiring a tool. The power switch 24 can be disposed on the back of the device 12, in the recess 23, so that the power switch 24 is completely covered by a support mechanism, and therefore completely inaccessible by any person, when mounted to the support mechanism. A battery cover 26, positioned below the power switch 24, for covering a battery compartment containing batteries for powering the device 12, can also be disposed in the recess 23, so that the batteries are also completely inaccessible by any person when mounted to the support mechanism.

In one aspect, the device 12 can provide an escalation protocol with respect to low battery conditions, particularly when alternating current (AC) power is disconnected from the power port 30. Approximate battery life for the escalation protocol can be determined by a processor or controller of the device 12 as described herein. Fully charged batteries may provide at least 30 days of continuous operation of the device 12. However, if the controller determines a first battery threshold is met, such as charge sufficient for only 3 days of operation or less, the controller can provide a corresponding first low battery indication, such as activating/illuminating the battery level indicator LED 20 (red). Next, if the controller determines a second battery threshold is met, such as charge sufficient for only 2 days of operation or less, the controller can provide a corresponding second low battery indication, such as an audio cue played to the speaker 16 (such as "Battery is low. Change battery now."), along with the battery level indicator LED 20 being turned on. In addition, during the second low battery indication, the aforementioned audio cue can be played back repeatedly in a given period, such as every 15 seconds. Finally, if the controller determines a third (lowest) battery threshold is met, such as near zero charge remaining, the controller can provide a corresponding third low battery indication, such as the battery level indicator LED 20 flashing to indicate a "dead battery mode" beacon with all monitoring being ceased.

Figure 3:
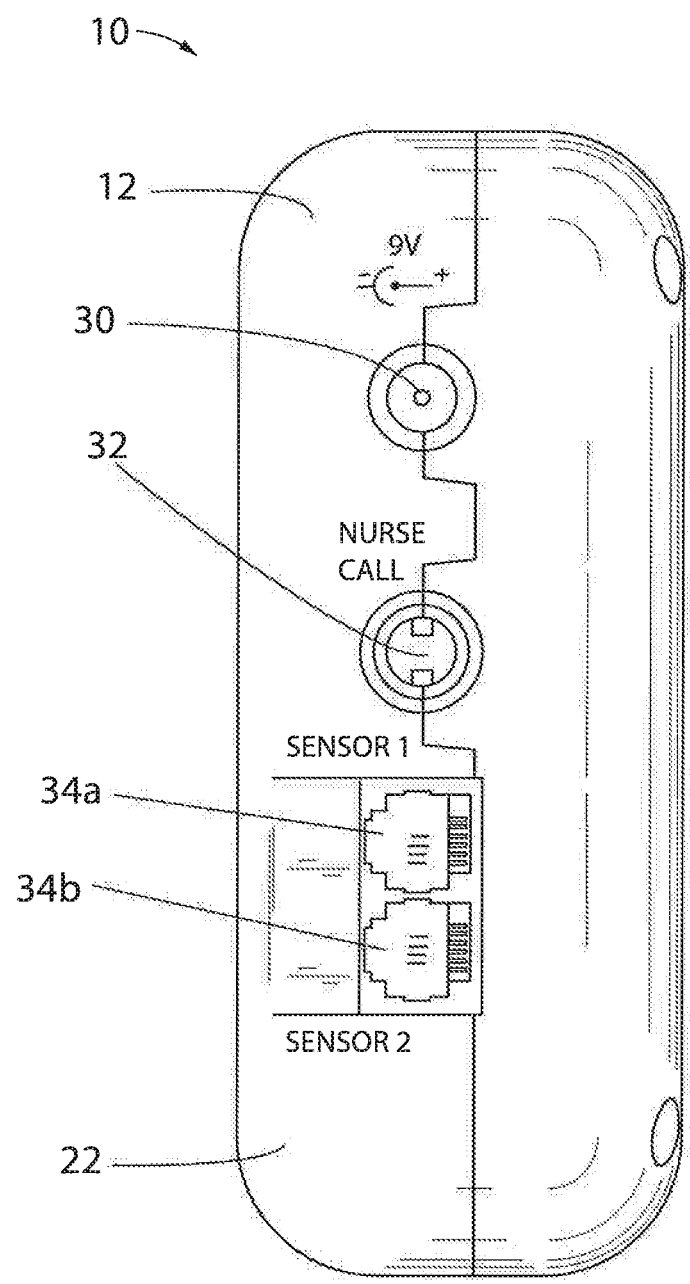
FIG. 3 is a first side view of the electronic fall monitoring system of FIG. 1.

As shown in the first side view of FIG. 3, the device 12 can include multiple wired and/or wireless connections or ports, including a power port 30 for connecting to a wired AC power source, a nurse call port 32 for connecting to a nurse's station (not shown), and multiple patient sensor ports 34, such as first and second sensor ports 34a and 34b, also identified as "Sensor 1" and "Sensor 2," respectively, which could comprise registered jack (RJ) connectors on the housing 22, such as RJ-12 connectors, for example, for individually connecting to patient sensors. Each sensor port 34 can be operable to connect to a patient sensor for detecting an activation and/or deactivation of the patient sensor. An activation of a patient sensor could occur, for example, when a patient rests on the sensor indicating a physical presence at the sensor. A deactivation of a patient sensor could occur, for example, when a patient later moves from the sensor, indicating a loss of physical presence at the sensor. In addition to monitoring for such activations and/or deactivations, each sensor port 34 can also be monitored for connections and/or disconnections to sensors. Accordingly, the nurse call port 32 and/or the patient sensor ports 34 can be configured for wired connections, such as by cabling directly to another device, or wireless connections, such as by cabling to a dongle comprising a radio and antenna, or a combination thereof. In addition, as will be described herein, the device 12 can further provide wireless connections to patient sensors and/or a nurse's stations through an internal wireless communications module comprising one or more radios and antennas, such as a near-field communication (NEC) and/or Bluetooth Low Energy (BLE) device. In one aspect, an internal wireless communications module may use out-of-band (OOB) pairing via NFC to establish a Bluetooth connection. In OOB pairing, public keys can be exchanged via a given wireless technology, such as NFC.

Figure 4:
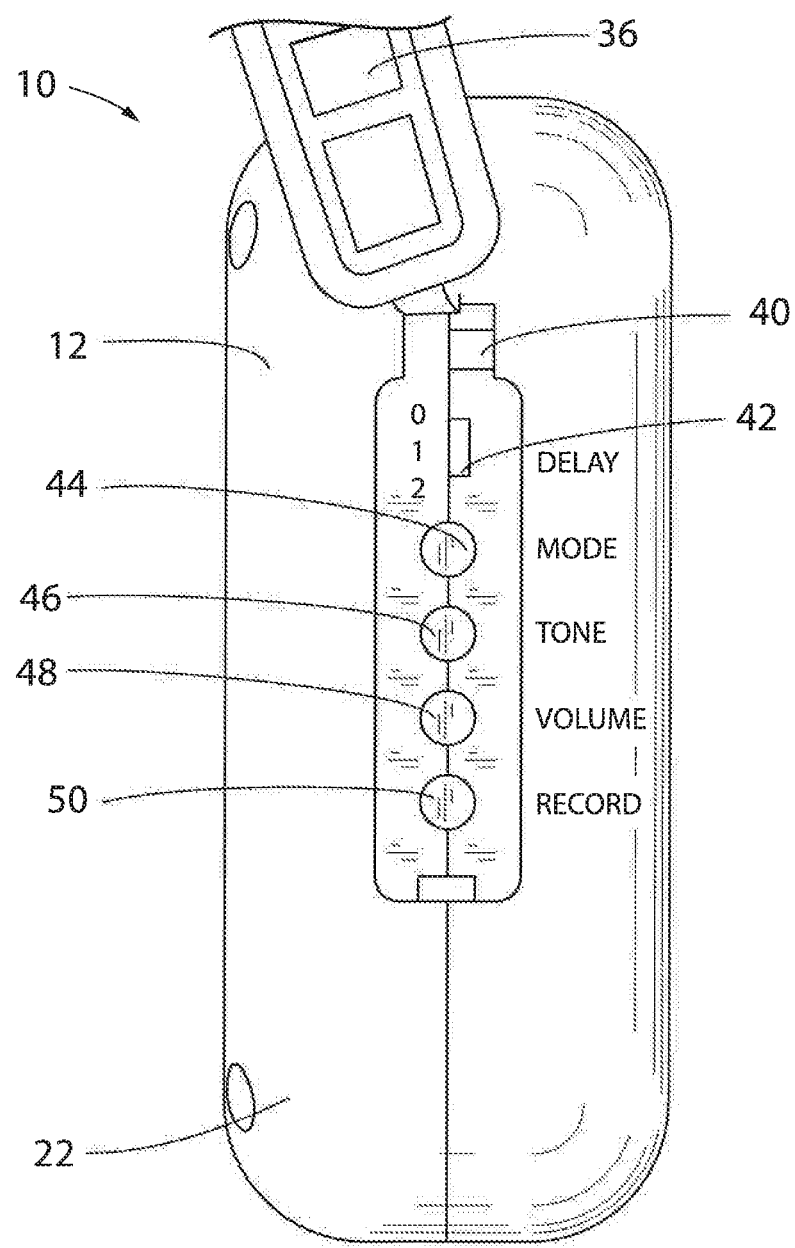
FIG. 4 is a second side view of the electronic fall monitoring system of FIG. 1.

As shown in the second side view of FIG. 4, the device 12 can include multiple configuration inputs for configuring the device 12. A housing cover 36 can cover or shield the configuration inputs when not in use. The configuration inputs can include, among other things: a sliding manual electric nurse call switch 40 for configuring the nurse call port 32 to operate normally open ("NO") or normally closed ("NC"); a sliding manual electric delay switch 42 for configuring a delay which must be met before a sensed deactivation at a patient sensor can cause an alarm, such as 0 (no delay), 1 second or 2 seconds; an alarm mode button 44 for configuring a type of alarm which occurs when a sensed deactivation at a patient sensor occurs, such as a playback of a recorded voice and an audible tone, playback of the recorded voice only, the audible tone only, or mute; a tone button 46 for configuring a different types of audible alarm tones, such as for distinguishing between different devices 12; a volume button 48 for configuring a volume of the alarm, such as low, medium or high; and/or a record button 50 for recording a voiced statement for playback during an alarm.

In one aspect, audio playback by the device 12 can be reset more efficiently and conveniently than past systems. In particular, when a user double presses the record button 50 in rapid succession (double click), the device 12 can immediately play an audio cue warning at the speaker 16 about the alarm recording being reset, such as "Alarm reset in 3 . . . 2 . . . 1 . . . ," followed by resetting/clearing any recorded audio message for the alarm to a default voice message of the device 12 for the alarm. This provides a simple way for users to reset the alarm message while keeping other device settings intact. This is an improvement over other systems, for example, which may require removal of all power sources, including batteries, and waiting for power to fully discharge, before resetting the alarm (which resets audio message and other settings).

In addition, in one aspect, audio playback by the device 12 can be responsive to differing changes in power states. In particular, when an AC power adapter is connected at the power port 30, the device 12 detects such connection and play "On wall cube power" at the speaker 16. Similarly, when AC power adapter is disconnected from the power port 30, the device 12 detects such disconnection and play "On battery power" at the speaker 16. This advantageously allows immediate notifications to the user upon changes in power states which may be accidental.

In addition, in one aspect, the device 12 can provide an audio cue playback associated with failsafe monitoring of a given sensor. A "failsafe" alarm may occur when a sensor signal is lost while in the monitor mode (monitoring a patient). When a failsafe alarm is triggered, the device 12 can detect such occurrence and play "Reconnect sensor" at the speaker 16. In addition, if a user selectable or standby input 54 is pressed for producing a hold, as described herein, the device 12 can again play "Reconnect sensor" at the speaker 16 as a failsafe, repeatedly, until the lost sensor signal is remedied, such as by replacing the sensor or powering off the alarm.

Figure 5:
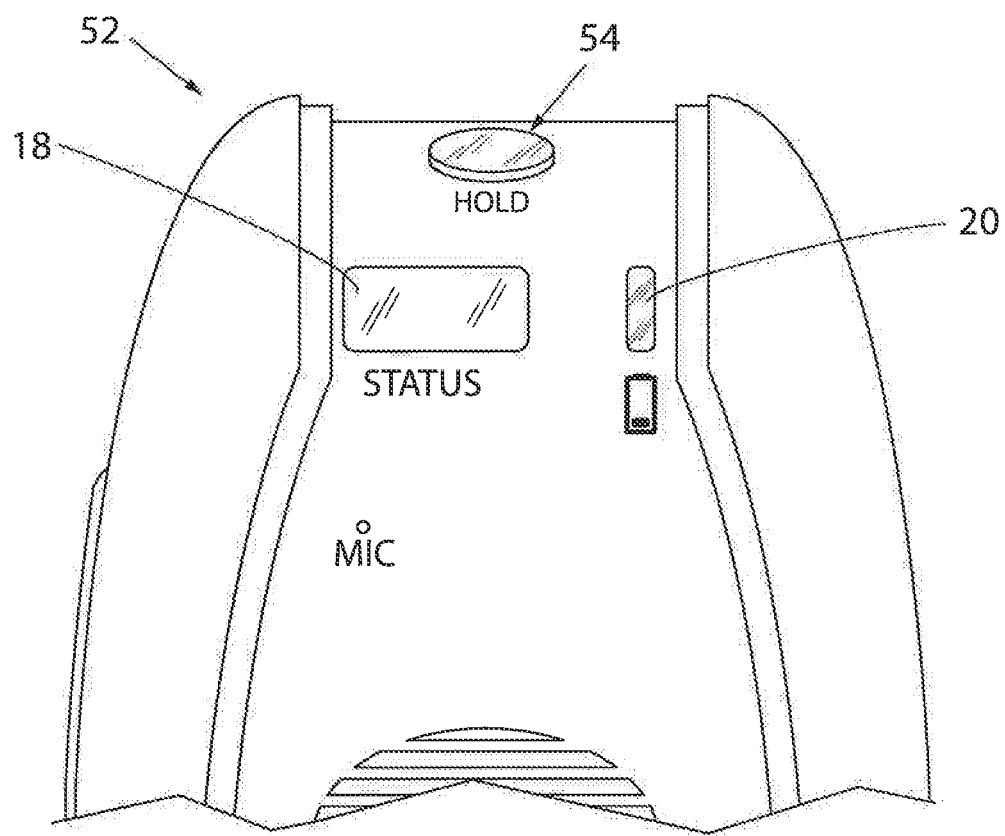
FIG. 5 is a detailed view illustrating a standby input and multi-color LED of the electronic fall monitoring system of FIG. 1.

As shown in FIG. 5, a detailed view 52 of the front of the device 12, the user selectable or standby input 54 (or "HOLD" button) can be prominently positioned proximal to the LED 18. The standby input 54 can operate when pressed, even momentarily, for a shorter duration, to temporary hold or suspend the device 12, from either the monitor mode or the alarm mode, to the standby mode. In addition, in one aspect, the standby input 54 can be wirelessly activated to achieve all standby/hold operations from various modes as described herein without requiring the user to physically press (or be near) the standby input 54. Accordingly, a "smart badge" comprising a Bluetooth beacon could be used in which, when the Bluetooth beacon comes in proximity of the device 12, the device 12 could be wirelessly commanded to enter standby mode via the standby input.

The standby input 54 can keep the device 12 in the standby mode for a predetermined amount of time, such as 30 seconds, each time the standby input 54 is pressed quickly or momentarily. When the standby input 54 is pressed for a longer duration, or predetermined minimum duration, such as at least 3 seconds, an extended (longer) hold or suspend can be commanded, such as 5 minutes or more. In one aspect, the standby input 54 can provide a singular button that pauses monitoring for a given time which is communicated to the user via the status light provided by LED 18 changing colors to red for a given time, after which the alarm and status light either begin monitoring if a patient is on the sensor or pad (green) or standby if no pressure is detected (yellow).

Referring now to FIGS. 6-14, in accordance with an aspect of the invention, a processor or controller of the device 12 as described herein can execute a program stored in a non-transient medium of the device 12 for accomplishing various modes of operation (apart from any particular alarm mode), including the aforementioned standby, monitor and alarms modes. In addition, the processor can control the LED 18 to illuminate a color corresponding to a given mode, which color and mode can change based on various conditions encountered, such as yellow for standby, green for monitor and red for alarm. In one aspect, a slow flashing yellow may indicate a "standby" mode in which the device 12 is ready to resume monitoring or awaiting the connection of a sensor input; a fast flashing yellow may indicate a a short delay or "buffer" mode before transitioning into the monitoring mode to allow continuous sensing for a minimum time, such as 3 seconds, to prevent false monitoring activation; a slow flashing green may indicate an actively monitoring mode; a slow flashing red may indicate a temporary hold mode (normal or extended) in which no monitoring occurs for a given period of time based on the standby input 54 or "hold button input;" and a fast flashing red may indicate an active "alarm" mode, typically accompanied by audio alerts and/or nurse call. The numerated steps in each figure are correspondingly highlighted to indicate the particular mode of the step (see "Status Light Key" shown in FIG. 6).

Figure 6:
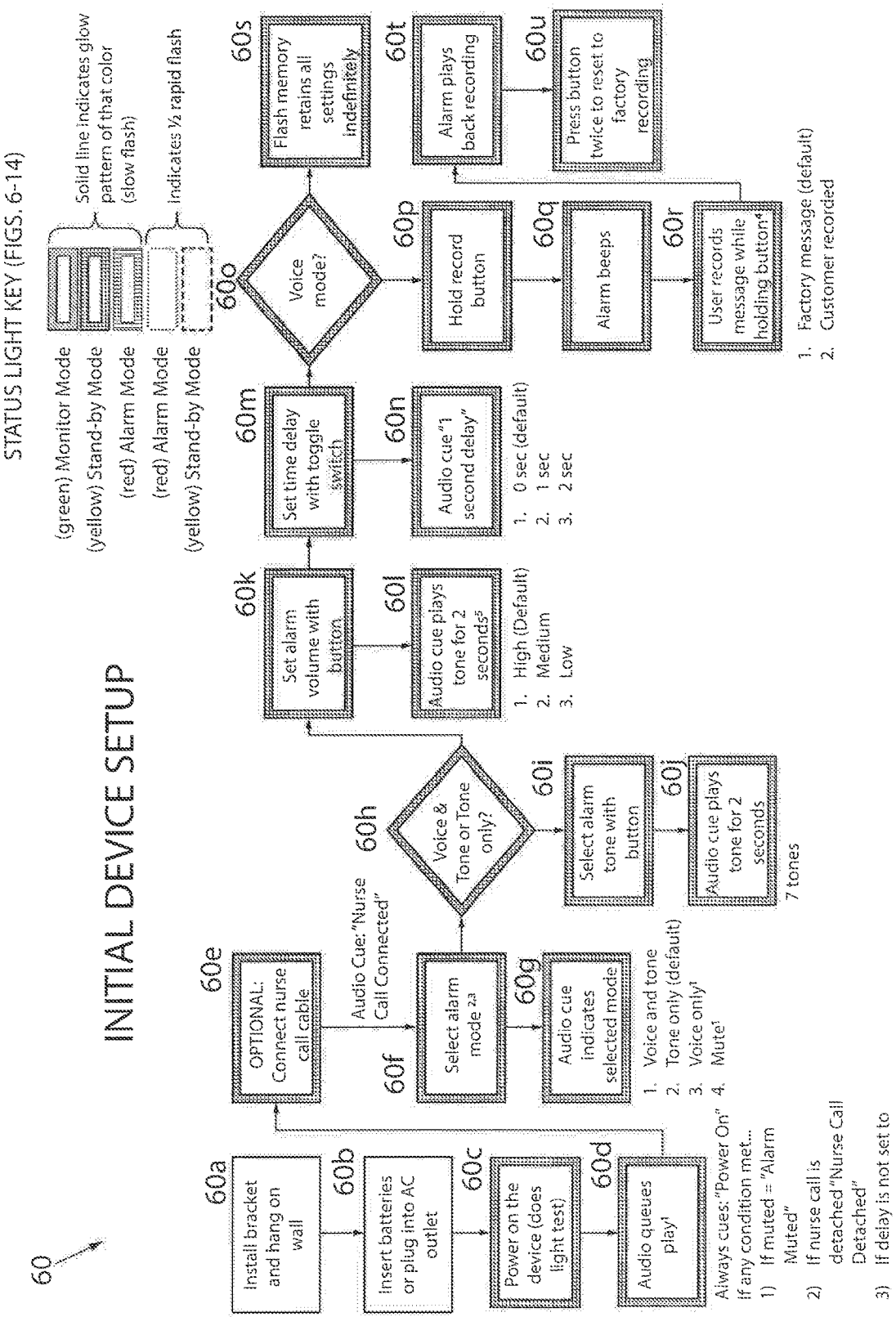
FIG. 6 is a flow chart illustrating initial set up with an electronic fall monitoring system in accordance with an aspect of the invention.

Referring to FIG. 6, a flow chart 60 illustrates an initial set up with the electronic fall monitoring system 10 in accordance with an aspect of the invention. At 60a, the device 12 can be installed in a support mechanism, such as a bracket, clip, bar or other arrangement, at the recess 23. At 60b-60c, batteries can be installed in the battery compartment, and/or AC power connected to the power port 30, turning on the device 12, bringing the device into the standby mode, and illuminating the LED 18 yellow. At 60d, an audio cue can play through the speaker 16 summarizing a current, default state to the user, such as "power on, alarm muted, nurse call disconnected, 1 second delay." At 60e, a nurse call cable can optionally be connected to the nurse call port 32 with the audio cue "Nurse Call Connected." At 60f, the user can select a desired alarm mode via the alarm mode button 44 (apart from any particular mode of operation). At 60g, an audio cue can play summarizing the selected alarm mode, such as "voice and tone," or "tone only." Following 60h, when voice and tone is selected, or when tone only is selected, at 60i the user can select a desired alarm tone via the tone button 46, followed by an audio cue playing the specified tone at 60j. Also, following 60h, when voice and tone is selected, or when tone only is selected, at 60k the user can select a desired alarm volume via the volume button 48, followed by an audio cue playing the tone at the specified volume 60l. At 60m, the user can select a desired delay which must be met before the alarm can activate, such as 0 (no delay), 1 second or 2 seconds, via the delay switch 42, followed by an audio cue playing summarizing the delay at 60n. Following 60o, when voice is selected as the desired alarm mode, at 60p-60u, the user can record a statement through the microphone 14, which could be played back through the speaker 16 when the alarm is activated, using the record button 50. At 60s, a non-volatile memory retains each of the aforementioned user settings. The device 12 can be in the standby mode (with the LED 18 illuminated yellow) through each of the aforementioned steps. Although many configurations are discussed above, the user can skip certain configurations and accept default values where skipped. In addition, a reset function can be received to clear user selections and restore the system to default values.

Figure 7:
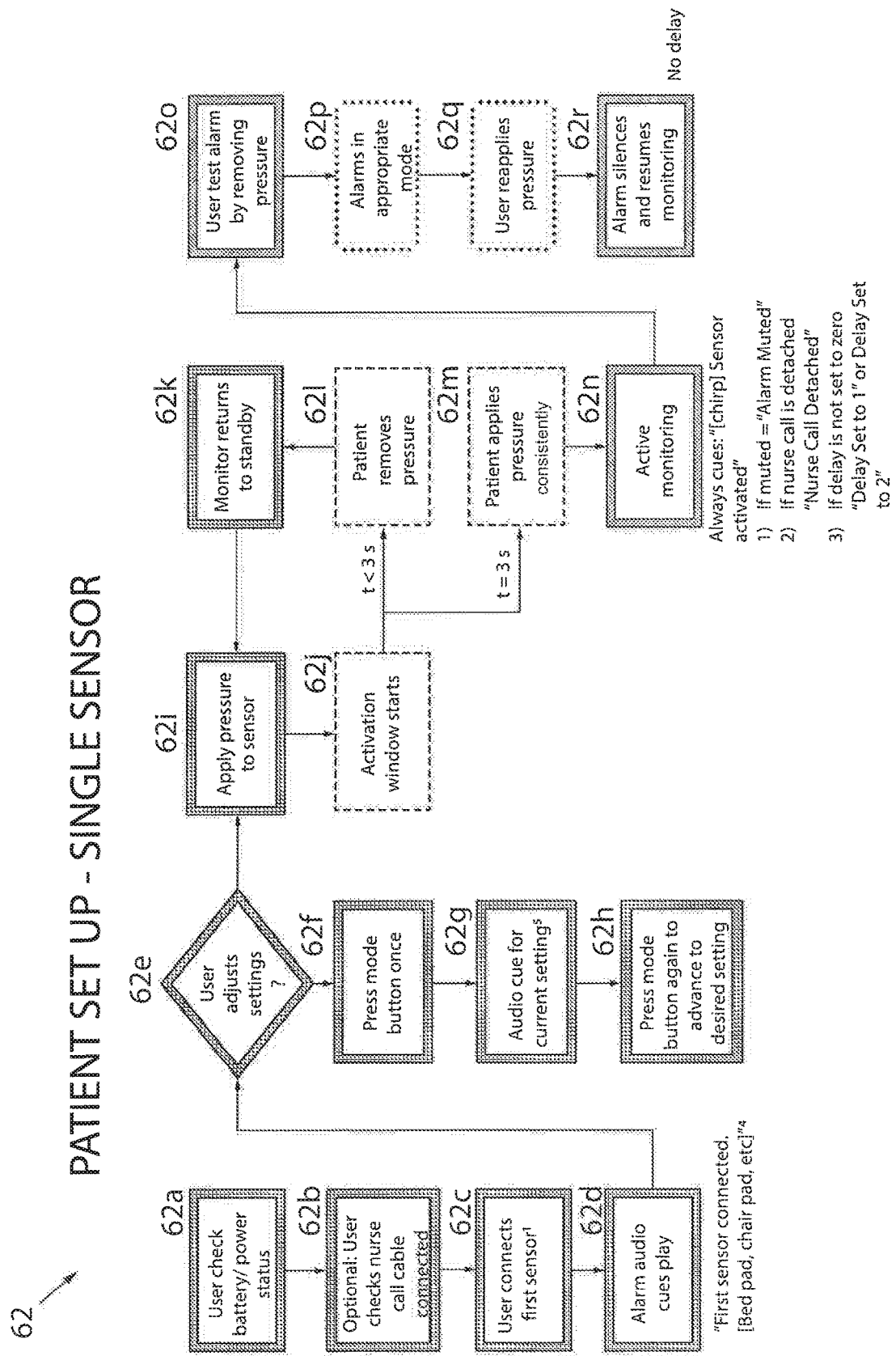
FIG. 7 is a flow chart illustrating single sensor set up with an electronic fall monitoring system in accordance with an aspect of the invention.

Referring to FIG. 7, a flow chart 62 illustrates a single patient sensor set up with the electronic fall monitoring system 10 in accordance with an aspect of the invention. In the standby mode, at 62a the user can check batter/power status, at 62b the user can check nurse cable connection status, at 62c the user can connect a first patient sensor to a first sensor port, such as first sensor port 34a, and at 62d an audio cue can play summarizing the sensor connection state, such as "first sensor connected." At 62e-62h, the user can configure the alarm settings to customize the alarm for the first patient sensor at the first sensor port. When additional patient sensors are connected, the user can similarly customize alarms for those sensors so as to distinguish alarms from among the sensors. The device 12 can be in the standby mode (with the LED 18 illuminated yellow) through each of the aforementioned steps. At 62i, the processor of device 12 can detect an activation of the sensor, upon an application of pressure or closing of a belt sensor on the sensor by the patient, indicating a physical presence at the sensor. At 62j, with the activation detected, the device 12 can transition to the monitor mode (with the LED 18 flashing yellow), and an audio cue can play summarizing the event and the current state, such as "sensor activation [beep], alarm muted, nurse call disconnected, 1 second delay." If at 62l a deactivation is detected within a predetermined amount of time, such as less than 3 seconds, the device 12 can return to the standby mode (the LED 18 illuminated yellow) at 62k, until another activation is detected at 62i. This provides hysteresis control. However, if at 62m the activation is maintained for at least the predetermined amount of time, such as 3 seconds or more, the device 12 can continue in the monitor mode (with the LED 18 illuminated green) at 62n. Then, if at 62o the patient removes pressure from the sensor with a deactivation detected, the device 12 can transition to the alarm mode (with the LED 18 flashing red) at 62p, with the selected alarm being active, until pressure is reapplied to the sensor at 62q to silence the alarm and resume monitoring in the monitor mode (with the LED 18 illuminated green) at 62r.

Figure 8:
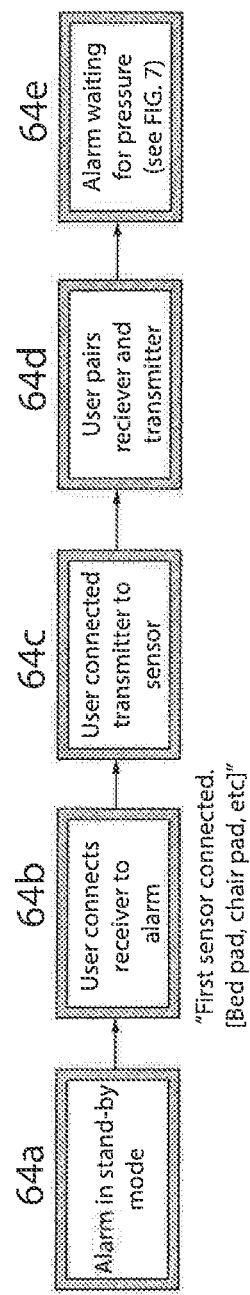
FIG. 8 is a flow chart illustrating wireless sensor set up with an electronic fall monitoring system in accordance with an aspect of the invention.

Referring to FIG. 8, a flow chart 64 illustrates a wireless sensor set up with the electronic fall monitoring system 10 in accordance with an aspect of the invention. While in the standby mode (the LED 18 illuminated yellow) at 64a-64e, a user can pair a wireless transmitter to wirelessly transmit the activation/deactivation events to a wireless receiver connected to a sensor port 34 of the device 12. Then, similar to the flow chart 62, the processor of device 12 can wirelessly detect an activation of the sensor, upon an application of pressure on the sensor by the patient, indicating a physical presence at the sensor, with active monitoring and hysteresis control.

Figure 9:
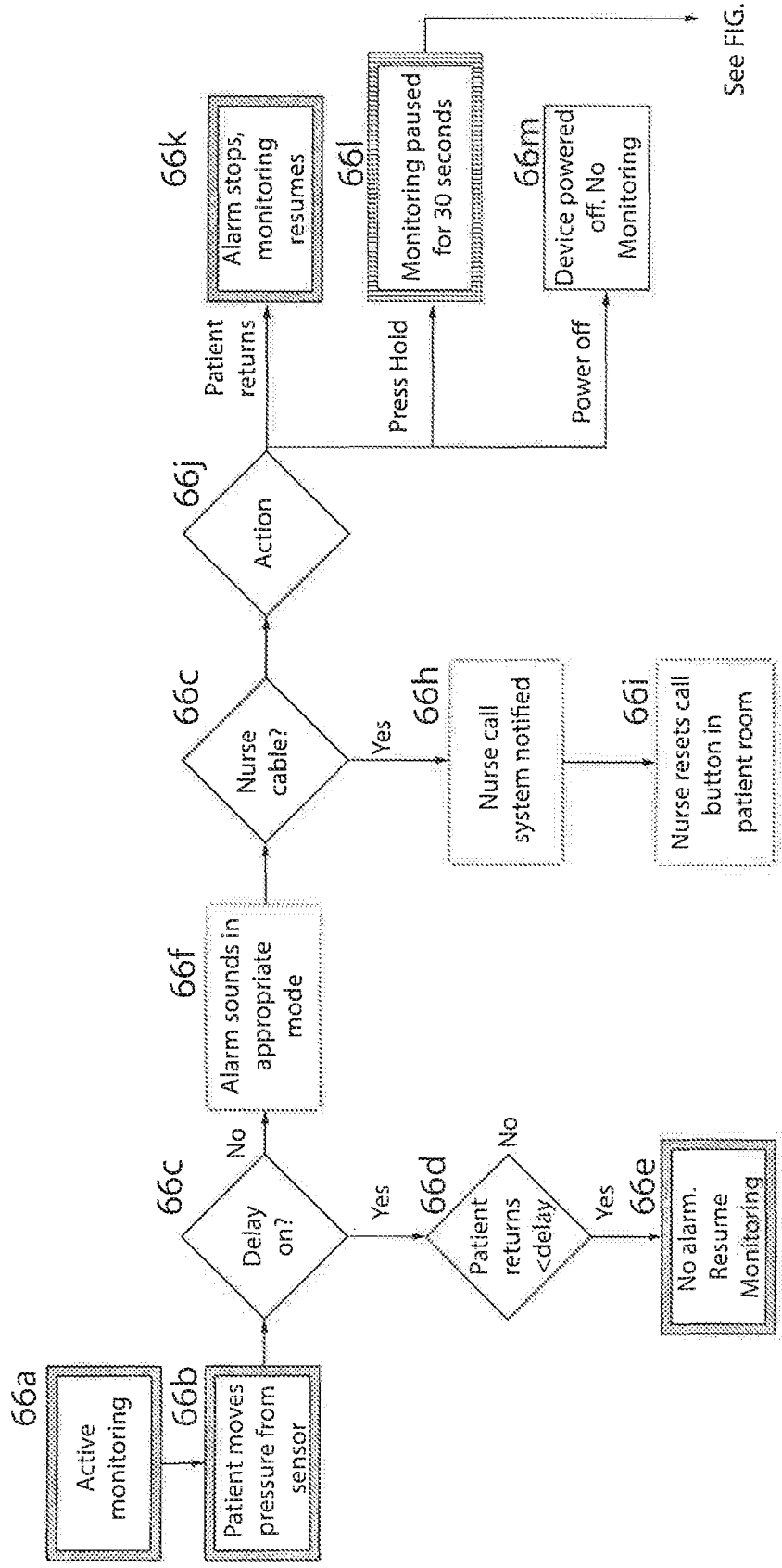
FIG. 9 is a flow chart illustrating single sensor monitoring with an electronic fall monitoring system in accordance with an aspect of the invention.

Referring to FIG. 9, a flow chart 66 illustrates monitoring in with the electronic fall monitoring system 10 with a single sensor, by way of example, in accordance with an aspect of the invention. While in the monitor mode (with the LED 18 illuminated green) at 66a, a deactivation is detected at 66b, the processor can determine with a delay has been set, via the delay switch 42, at 66c. If a delay has been set (Yes), at 66d, the processor can determine whether a re-activation is detected (the patient promptly returns to the sensor) within the time period allowed by the delay. If the re-activation is detected, with the patient returning to the sensor within the time period allowed by the delay (Yes), the device 12 does not enter the alarm mode, but rather continues in the monitor mode (with the LED 18 illuminated green). However, if at 66c a delay was not set (No), or if at 66d the re-activation does not occur, with the patient failing to return to the sensor within the time period allowed by the delay (No), at 66f the device 12 can transition to the alarm mode (with the LED 18 flashing red). At 66g, if a nurse cable is connected, the nurse call station will be notified for action at 66h-66i (with the LED 18 flashing red). At 66j, the processor can analyze several actions for proceeding. At 66k, if a re-activation is detected, with the patient returning to the sensor, the device 12 can transition back to the monitor mode (with the LED 18 illuminated green). Alternatively, if at 66j the standby input 54 is pressed, the device 12 can transition to the standby mode (the LED 18 illuminated red) at 66l, and with additional reference to FIG. 10A, when a re-activation is detected, with the patient returning to the sensor, the device 12 can transition back to the monitor mode (with the LED 18 illuminated green) at 68a. If at 66m the device is powered off, such as by turning the power switch 24 off, the device 12 will be turned off completely with no monitoring or illumination of the LED 18.

Figure 10A:
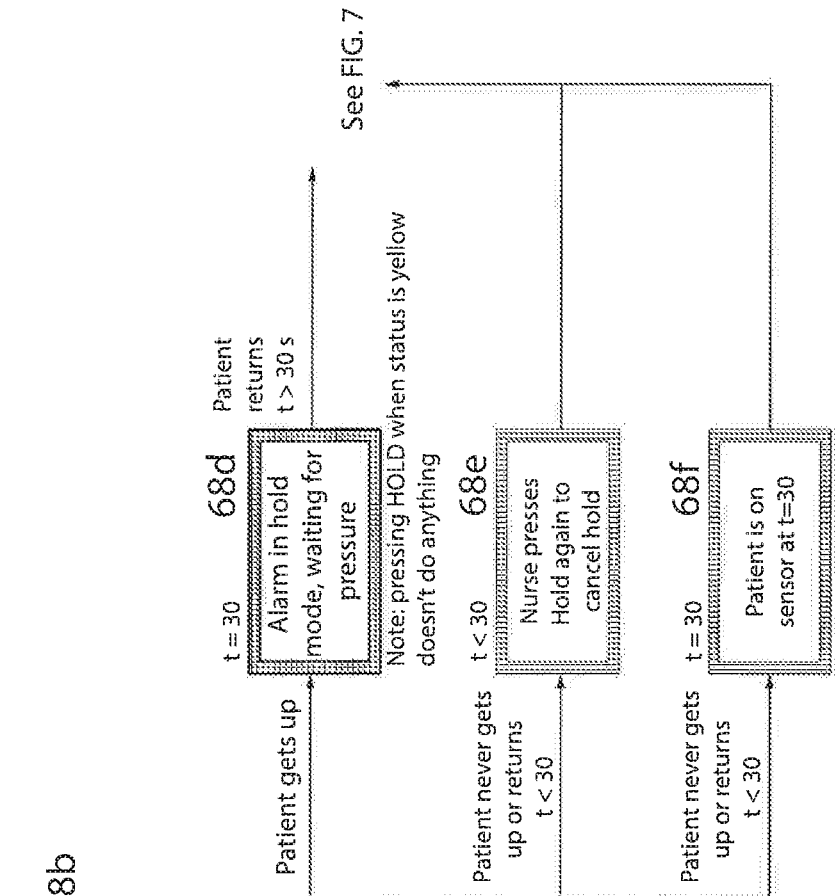
FIG. 10A is a flow chart illustrating single sensor monitoring and hold with an electronic fall monitoring system in accordance with an aspect of the invention.

Referring to FIG. 10A, a flow chart 68 illustrates single sensor monitoring and hold with the electronic fall monitoring system 10 in accordance with an aspect of the invention. While in the monitor mode (with the LED 18 illuminated green) at 68a, a user can press the standby input 54 at 68b for a first duration, such as less than 3 seconds, to transition to the alert mode (the LED 18 illuminated red) at 68c for a predetermined amount of time, such as 30 seconds or less. In one aspect, while in the alert mode, the processor can analyze several actions for proceeding. At 68d, if a deactivation is detected within the predetermined amount of time, such as less than the 30 seconds, the LED 18 can illuminate yellow, and the device 12 can move to the standby mode until returning to the monitor mode (see FIG. 7). Also, at 68e, if a deactivation is not detected within the predetermined amount of time, with the LED 18 remaining red, the user can press the standby input 54 again, to clear the delay as needed, returning to the monitor mode (see FIG. 7). Regardless, at 68f, if an activation (or re-activation) is detected when the predetermined amount of time expires, such as at the 30 seconds, the device 12 can return to the monitor mode (see FIG. 7). Then, according to the flow chart 62, the processor of device 12 can continue with active monitoring and hysteresis control.

Referring to FIG. 10B, a flow chart 69 illustrates single sensor monitoring and extended hold with the electronic fall monitoring system 10 in accordance with an aspect of the invention. While in the monitor mode (with the LED 18 illuminated green) at 69a, a user can press the standby input 54 at 69b for a second duration, such as more than 3 seconds, to transition to the alert mode (the LED 18 illuminated red) at 69c for an extended predetermined amount of time, such as 5 minutes or more. In one aspect, while in the alert mode, the processor can analyze several actions for proceeding. At 69d, and referring again to FIG. 7, if a deactivation is detected within the extended predetermined amount of time, such as less than the 5 minutes, the LED 18 can illuminate yellow, and the device 12 can move to the standby mode until returning to the monitor mode (see FIG. 7). Also, at 69e, if a deactivation is not detected within the extended predetermined amount of time, with the LED 18 remaining red, the user can press the standby input 54 again, to clear the delay as needed, returning to the monitor mode at (see FIG. 7). Regardless, at 69f, if an activation (or re-activation) is detected when the extended predetermined amount of time expires, such as at the 5 minutes, the device 12 can return to the monitor mode at (see FIG. 7). Then, according to the flow chart 62, the processor of device 12 can continue with active monitoring and hysteresis control.

Figure 11:
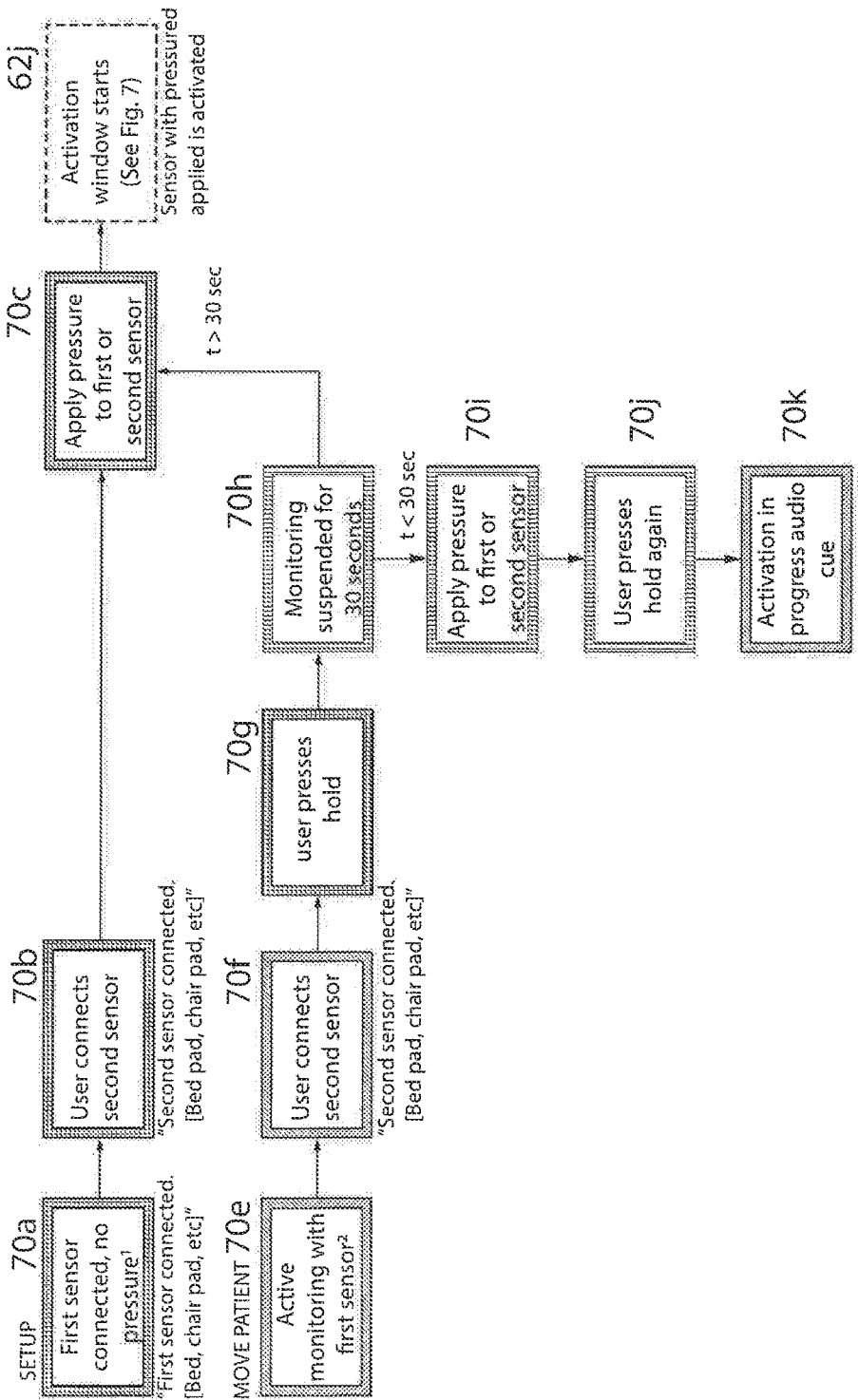
FIG. 11 is a flow chart illustrating dual sensor set up with an electronic fall monitoring system in accordance with an aspect of the invention.

Referring to FIG. 11, a flow chart 70 illustrates a multi sensor set up with the electronic fall monitoring system 10 in accordance with an aspect of the invention. At 70a, in the standby mode, a user can connect a first patient sensor (such as to the first sensor port 34a) with a first corresponding audio cue being played, and at 70b the user can connect a second patient sensor (such as to the second sensor port 34b) with a second corresponding audio cue being played. At 70c, the processor of device 12 can detect an activation of a sensor, either the first sensor or the second sensor, and correspondingly transition to 62j (with the LED 18 flashing yellow) (see FIG. 7), monitoring such first or second sensor. In other words, multiple sensors can be connected while in the standby mode, but not until one of the sensors is activated will the device 12 enter the monitor mode. In another path, at 70e the device 12 may already be in the monitor mode (with the LED 18 illuminated green), actively monitoring the first patient sensor (which may be connected to the first sensor port 34a). Then, at 70f, a user can freely connect a second patient sensor (such as to the second sensor port 34b) with a second corresponding audio cue being played, still in the monitor mode. To adjust the patient from one sensor to the other, at 70g a user can press the standby input 54 (the LED 18 illuminated yellow), which can transition the device 12 to the alert mode (the LED 18 illuminated red) at 70h for the predetermined amount of time, such as 30 seconds. Still in the alert mode, at 70i, the patient can apply pressure to either the first or second sensor, and at 70j the user can press the standby input 54 again, to clear the delay as needed. At 70k, temporary transition to the alert mode can then expire, returning to the monitor mode (with the LED 18 illuminated green). At 70c and 62j, monitoring resumes for the sensor on which pressure was applied at 70i. In other words, using the standby input 54, a patient can be transitioned from one sensor to the next.

Figure 12:
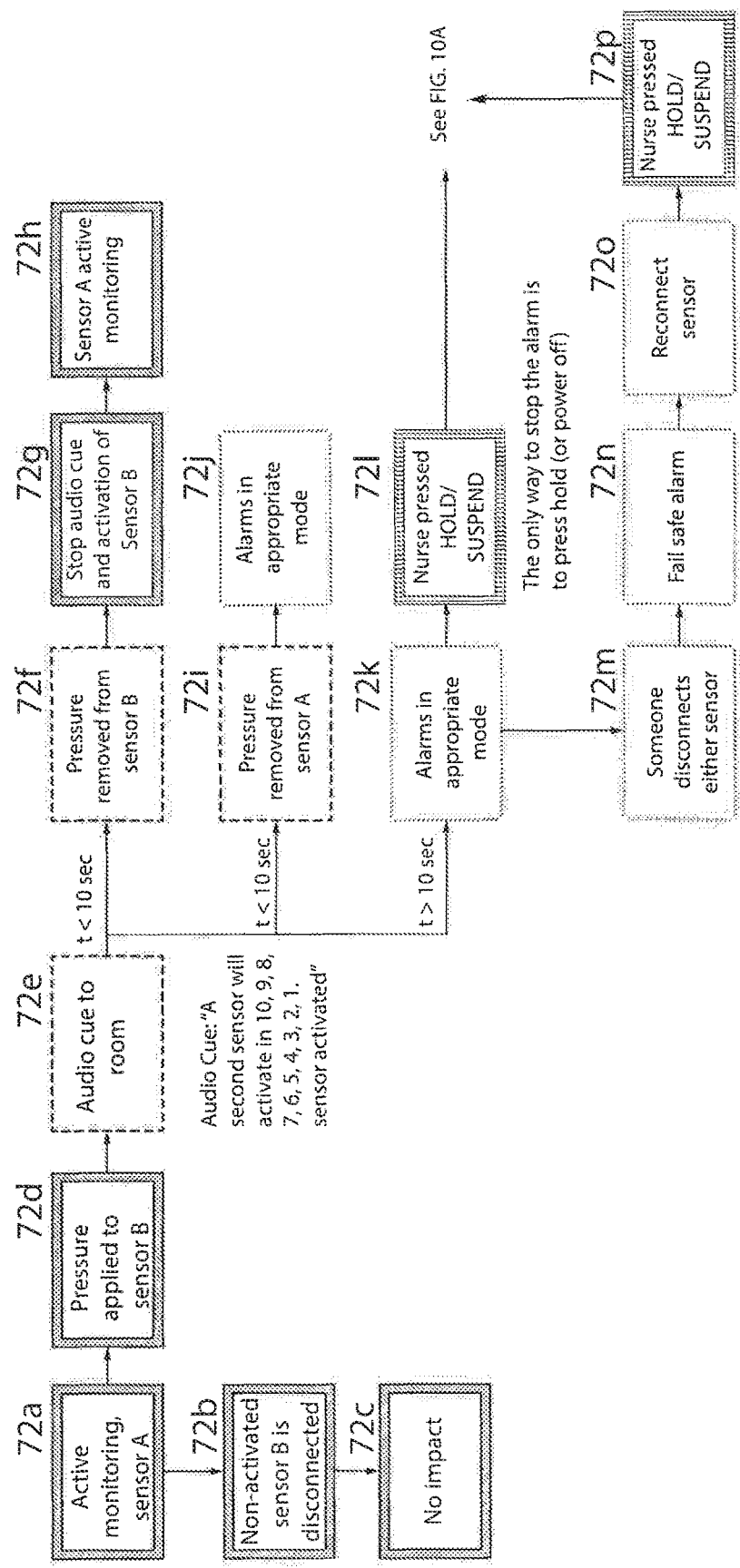
FIG. 12 is a flow chart illustrating dual sensor monitoring with an electronic fall monitoring system in accordance with an aspect of the invention.

Referring to FIG. 12, a flow chart 72 illustrates multi sensor monitoring with the electronic fall monitoring system 10 in accordance with an aspect of the invention. At 72a, a first patient sensor (which may be connected to the first sensor port 34a) (also "sensor A" or "primary sensor") can be monitored by the device 12 in the monitor mode (with the LED 18 illuminated green) while a second patient sensor (which may be connected to the first sensor port 34b) (also "sensor B" or "secondary sensor") is also connected. At 72b, the second patient sensor can be disconnected. However, despite such disconnection, the device 12 continues monitoring the primary patient sensor at 72c in the monitor mode without any impact. At 72d, the processor can detect an activation of the second patient sensor. At 72e, the device can transition to the standby mode (with the LED 18 flashing yellow) and an audio cue can play a warning with a countdown corresponding to a predetermined amount of time, such as "A second sensor will activate in 10, 9, 8, 7, 6, 5, 4, 3, 2, 1." In one aspect, a signal can also be sent to the nurse call station at 72e. At 72f, upon detecting a deactivation at the second patient sensor within the predetermined amount of time, the device 12 can simply transition back to the monitor mode (with the LED 18 illuminated green) and cease playing the warning at 72g, while continuing to monitor the first patient sensor in the monitor mode at 72h. In other words, multiple sensors can be connected while in the monitor mode, but only one sensor will be monitored, the one sensor being the sensor originally causing entry into the monitor mode. Alternatively, at 72i upon detecting a deactivation at the first patient sensor within the predetermined amount of time, the device 12 can transition to the alert mode (with the LED 18 flashing red) at 72j until resolved. Alternatively, at 72k upon expiration of the predetermined amount of time without any action, the device 12 can transition to the alert mode (with the LED 18 flashing red) at 72k. This can continue until the standby input 54 is pressed to stop the alarm at 72l, with the device 12 transitioning back to the monitor mode (with the LED 18 illuminated green) at 68a. However, if at 72k either the primary or secondary patient sensor is disconnected, the device 12 can transition to a fail-safe alarm at 72n. This can continue until the disconnected sensor(s) is/are reconnected. The alarm mode can continue until the standby input 54 is pressed to stop the alarm at 72p, with the device 12 transitioning back to the monitor mode (with the LED 18 illuminated green) at 68a.

Figure 13:
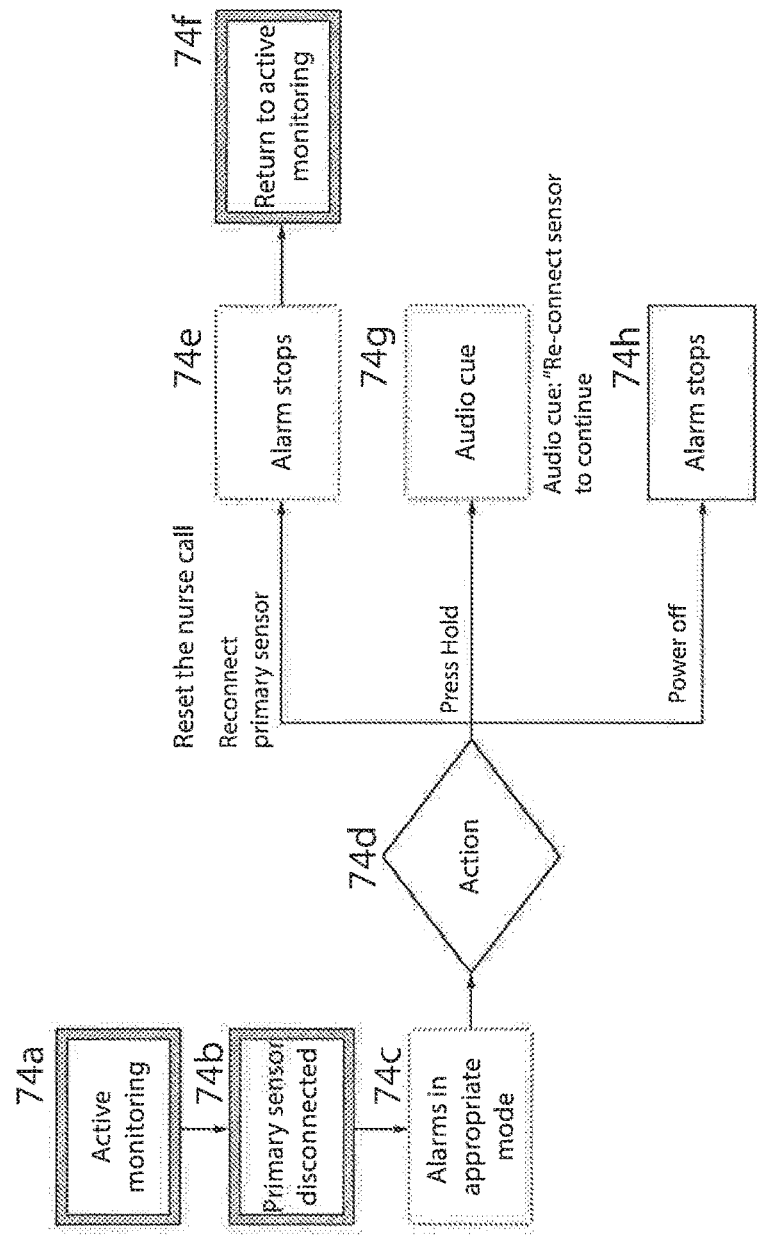
FIG. 13 is a flow chart illustrating sensor error modes with an electronic fall monitoring system in accordance with an aspect of the invention.

Referring to FIG. 13, a flow chart 74 illustrates sensor error modes with the electronic fall monitoring system 10 in accordance with an aspect of the invention. At 74a, while actively monitoring a first patient sensor (which may be connected to the first sensor port 34a) (also "sensor A" or "primary sensor") in the monitor mode (with the LED 18 illuminated green), a disconnection of the first patient sensor at 74b can cause a transition to the alarm mode (the LED 18 flashing red) at 74c. In such an instance, at 74d, the processor can analyze several actions for proceeding. At 74e, a re-connection of the first sensor can transition back to the monitor mode (with the LED 18 illuminated green) at 74f. Alternatively, if at 74g the standby input 54 is pressed, the device 12 can play an audio cue while in the alarm mode, such as "re-connect sensor to continue." Alternatively, if at 74h the device is powered off, such as by turning the power switch 24 off, the device 12 will be turned off completely with no monitoring or illumination of the LED 18.

Figure 14:
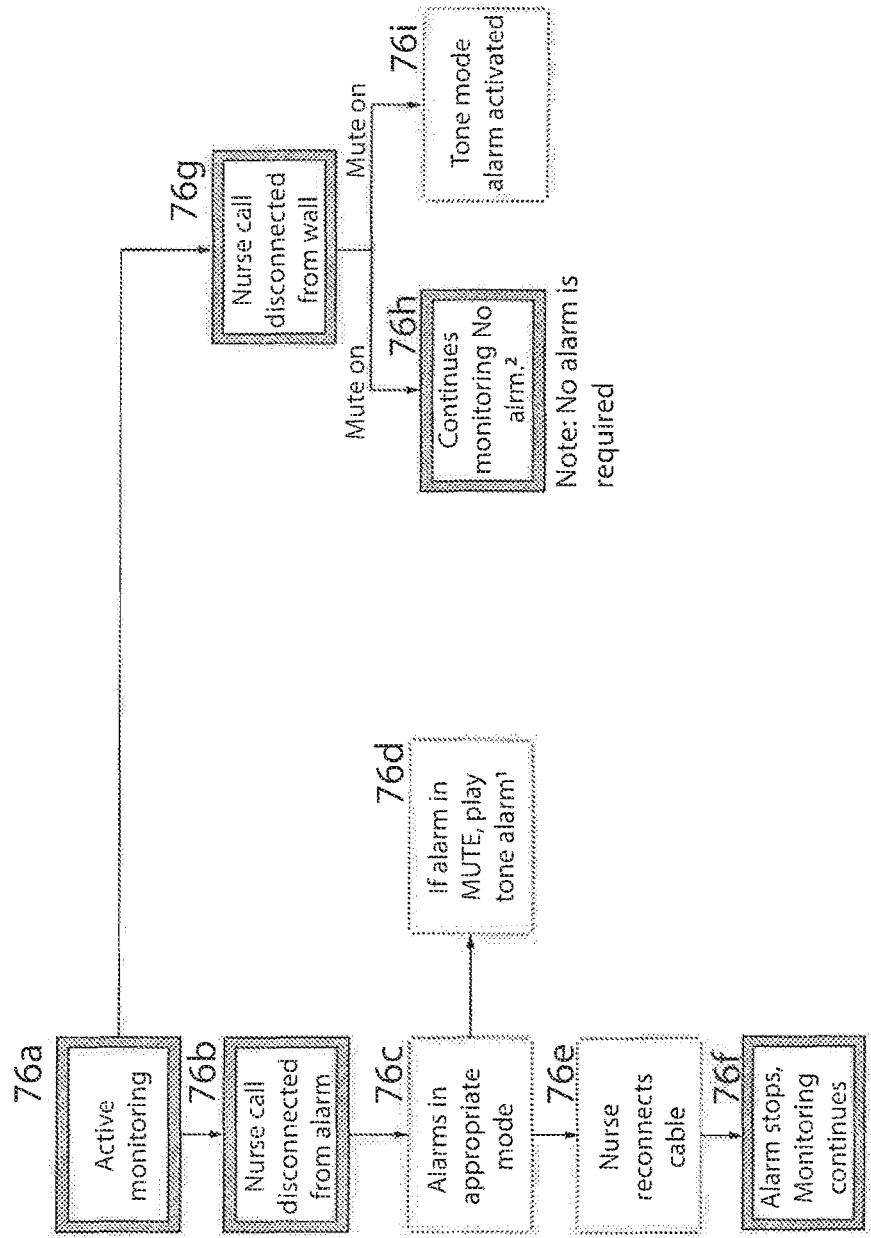
FIG. 14 is a flow chart illustrating nurse call error modes with an electronic fall monitoring system in accordance with an aspect of the invention.

Referring to FIG. 14, a flow chart 76 illustrates nurse call error modes with the electronic fall monitoring system 10 in accordance with an aspect of the invention. At 76a, while actively monitoring a patient sensor in the monitor mode (with the LED 18 illuminated green), the processor of the device 12 can detect a disconnection of the nurse call port 32 from the device itself at 76b. This can cause a transition to the alarm mode (the LED 18 flashing red) at 76c. If the alarm is in mute, the device 12 can play a tone alarm at 76d. The alarm mode will continue until the nurse call port 32 is re-connected at 76e, at which point the device 12 will return to the monitor mode (with the LED 18 illuminated green) at 76f. However, while actively monitoring the patient sensor in the monitor mode (with the LED 18 illuminated green) at 76a, if the processor of the device 12 instead detects a disconnection of the nurse call port 32 from the wall at 76g (with a cable still attached to the device itself at the nurse call port 32), the processor can determine whether the alarm is muted. If the alarm is not muted ("mute off"), the device 12 can continue to monitor the patient sensor in the monitor mode (with the LED 18 illuminated green) at 76h. However, if the alarm is muted ("mute on"), the device 12 can transition to the alarm mode (the LED 18 flashing red) at 76i. In addition, or alternatively, at 76i, if the alarm is muted ("mute on"), the device 112 can play an audio cue warning indicating "nurse call detached," and/or can cease muting ("mute off").

Many different audio cues can advantageously be played to correspond with various states and modes of the system as described above, including with respect to steps of FIGS. 6-14. Audio cues can include, for example: "ALARM RESET," "POWER ON," "BEGIN RECORD," "END RECORD," "VOLUME LOW," "VOLUME MEDIUM," "VOLUME HIGH," "TONE MODE," "VOICE MODE," "VOICE AND TONE MODE," "MUTE MODE," "SENSOR ONE ATTACHED," "SENSOR TWO ATTACHED," "SENSOR ONE ACTIVATED," "SENSOR TWO ACTIVATED," "SENSOR DETACHED," "TWO SENSORS IN USE," "PLEASE DON'T GET UP, SIT BACK DOWN AND USE THE CALL," "BUTTON TO CALL FOR HELP," "ZERO DELAY," "ONE SECOND DELAY," "TWO SECOND DELAY," "NURSE CALL ATTACHED," "NURSE CALL DETACHED," "LOW BATTERY," "FAILED SELF TEST," "AC ADAPTER CONNECTED," "AC ADAPTER DISCONNECTED," "PATIENT MONITORING RESUMED," "YOU HAVE ACTIVATED A SECOND SENSOR, PLEASE REMOVE PRESSURE WITHIN 10 SECONDS," and/or "ALARM SUSPEND." A default alarm message could comprise the following audio cue: "PLEASE DON'T GET UP. SIT BACK DOWN AND USE THE CALL BUTTON TO CALL FOR HELP." Such audio cues can be correspondingly played in the steps above as appropriate to give user guidance.

Accordingly, audio cues can be provided during various conditions, states and/or modes of the device 12, including as described above with respect to FIGS. 6-14. Such audio cues can provide cautions and/or gentle reminders at various times depending on severity. Audio cues providing cautions (more severe) may include, for example: a nurse call being detached, physically or virtually, a mute mode activated, and/or a delay set, such as 1 or 2 seconds, any of which occurring following power on and activation; an extended hold being activated (such as a 5 minute hold activated by pressing the standby input 54 for more than 3 seconds); a low battery detected (which may alert audio cues periodically, such as every 15 seconds, when power is below a critical level or threshold); power being disconnected from the power port 30; and/or a second sensor activation being detected, including with a second by second countdown which may start from 10. Audio cues providing gentle reminders (less severe) may include, for example: upon power on; a sensor being connected; a sensor being disconnected; a sensor being activated; and/or changes to given settings, such as delay, mode and/or volume.

Also, the device 12 can provide a "one step transfer" in which a caregiver may simply press the standby input 54 ("HOLD") once to transfer a patient from a first sensor to a second sensor, such as from a sensor arranged in a bed to a sensor arranged in a chair. Also, the device 12 can be selectively configured to latch an alarm, meaning an active alarm mode can continue even if the alarm condition causing the alarm mode is satisfied and no longer occurring (such as a patient returning to a sensor), or not latch the alarm, meaning an active alarm mode can stop when the alarm condition causing the alarm mode is satisfied and no longer occurring (such as the patient returning to the sensor).

Figure 15:
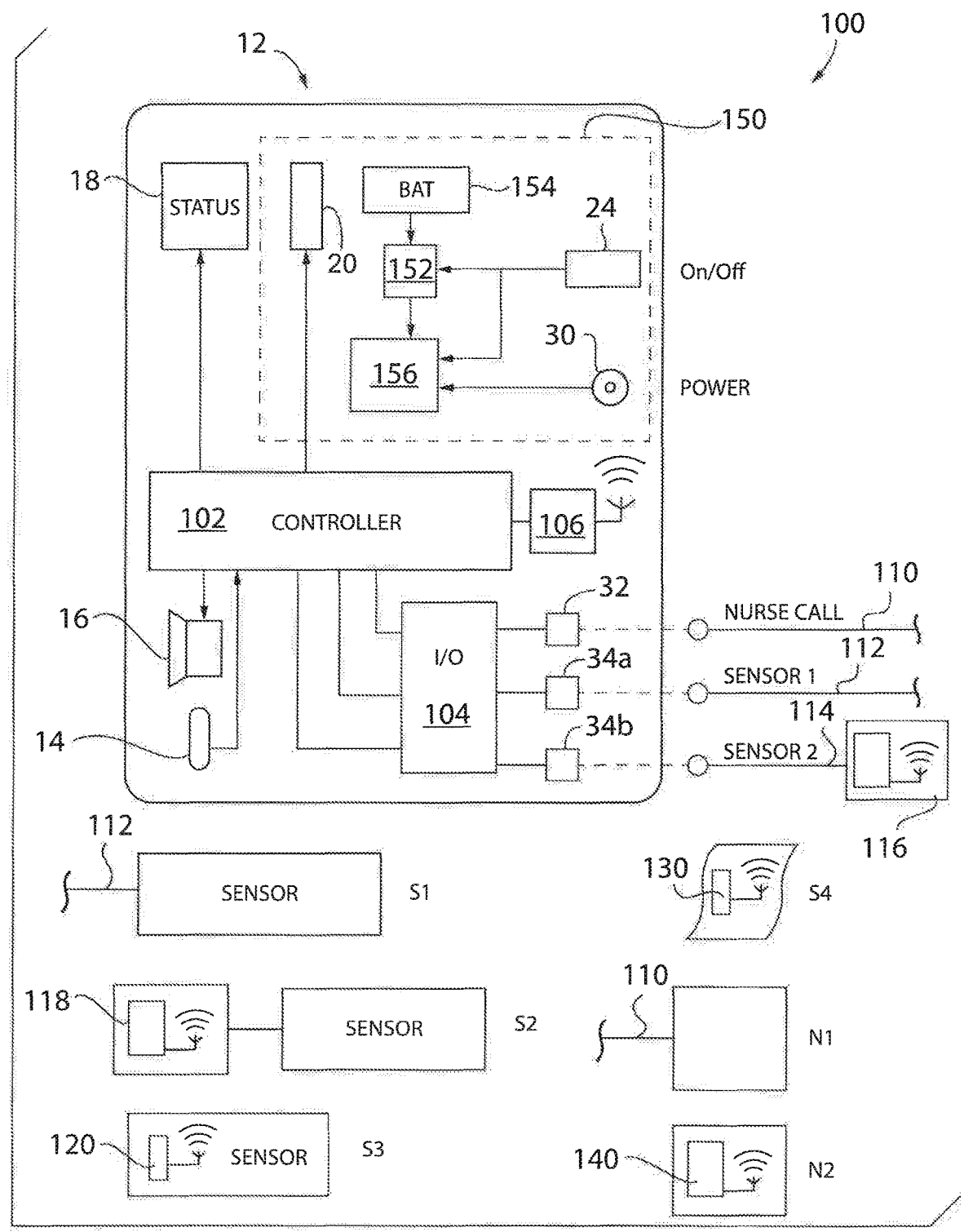
FIG. 15 is a diagram illustrating a system for electronic fall monitoring in accordance with an aspect of the invention.

Referring now to FIG. 15, a diagram illustrating a system 100 for electronic fall monitoring is provided in accordance with an aspect of the invention. In the system 100, a device 12 can connect to multiple patient sensors, such as patient sensors S1-S4, and/or multiple nurse call stations, such as nurse call stations N1-N2. Sensors S1-S3 could be sensors pads configured for chairs, beds or toilets and/or alarm belts. Sensor S4 could be a patient wearable device, such as a leg or arm band. Sensors S1-S4 can indicate, for example, presence or absence of a patient on the sensor, and for enhanced sensors, data about the patient, such as a patient's position, relative patient movement, a patient's movement between zones, and/or rate of patient movement.

The device 12 can include physical connection ports located on the housing 22, such as the nurse call port 32 and/or the first and second sensor ports 34a and 34b, respectively, as well as wireless connection ports (virtual) integrated within the housing 22. Such physical connection ports can be controlled by a processor or controller 102, which may include a microprocessor, microcontroller and/or programmable logic, and which may include non-volatile memory for storing conditions, states and/or modes of the device 12, including as described above with respect to FIGS. 6-14, interfacing with the physical connection ports through input/output (I/O) circuitry 104.

Connections to the physical connection ports may be wired from the device 12 to a patient sensor or nurse call station, such as wired connection 110 or cabling between the nurse call port 32 and nurse call station N1 and wired connection 112 or cabling between the first sensor port 34a and patient sensor S1. In addition, connections to the physical connection ports may also be wireless from the device 12 to a patient sensor or nurse call station through the use of a wired dongle, a small device able which can be connected to and used with the device 12 to allow wireless radio communications with other devices such as patient sensors and nurse call stations. For example, a wired connection 114 or cabling between the second sensor port 34b and a wireless dongle 116 associated with the device 12 can enable wireless communication with a compatible wireless patient sensor, such as a wireless sensor device 118, configured to communicate with the wireless dongle 116, associated with wireless patient sensor S2.

In addition, fully wireless connection ports (virtual) can be controlled by a wireless module 106, completely internal to the housing 22, which module is, in turn, controlled by the controller 102. The wireless module 106 could comprise one or more devices configured for one or more wireless communications protocols, such as near-field communication (NFC), radio-frequency identification (RFID) and/or Bluetooth, using one or more fully integrated antennas. For example, a first fully wireless virtual connection can be established via RFID between an element of the wireless module 106 and a wireless module 120, configured to communicate with the wireless module 106, associated with fully wireless patient sensor S3; a second fully wireless virtual connection can be established via Bluetooth between an element of the wireless module 106 and a wireless module 130, configured to communicate with the wireless module 106, associated with wearable patient sensor S4, which sensor is wearable as described herein; and a third fully wireless virtual connection can be established via NFC between an element of the wireless module 106 and a wireless module 140, configured to communicate with the wireless module 106, associated with a portable nurse call station device N2. Connections to wireless connection ports can be in addition to, or in alternative to, the aforementioned connections to physical connection ports. Connections to wireless connection ports can be established by initially bringing the wireless patient sensor S3, the wearable patient sensor S4 or the portable nurse call station device N2 in proximity to the device 12 and initiating an over-the-air handshaking protocol between the devices. Wireless connection initiation, progress and/or success can be indicated to the user through playback of corresponding audio cues through the speaker 16 and/or signaling of the LED 18.

In addition, the device 12 can include a power supply block 150 configured to eliminate trickle current drain or leakage from the batteries, reduce the incidence of corrosion at terminals of the batteries caused by such leakage, and prolong overall life of the device 12 (see also FIG. 2 illustrating battery cover 26 for retaining the batteries and power switch 24, and FIG. 3 illustrating power port 30 for receiving wired power). In particular, an isolation switch 152, comprising one or more transistors, is associated with power switch 24 to completely isolate power from batteries 154 before current from such batteries can reach power supply circuit 156. Power supply circuit 156, which can receive power from power port 30, and/or batteries 154 when enabled, provides power distribution to electrical components of the device 12, such as microphone 14, speaker 16, LED 18, LED 20, controller 102, I/O circuitry 104 and wireless module 106. When the power switch 24 is switched to "On" by a user, the isolation switch 152 is switched to allow power from the batteries 154 to conduct to the power supply circuit 156. In addition, the isolation switch 152 allows power from the power supply circuit 156 to distribute power to the aforementioned electrical components. However, when the power switch 24 is switched to "Off" by the user, the isolation switch 152 completely isolates batteries 154 and prevents power from batteries 154 from conducting to the power supply circuit 156. Unless power is provided through the power port 30, "Off" completely isolates electrical power from all components of the device 12. Nevertheless, conditions, states and/or modes of the device 12, including as described above with respect to FIGS. 6-14, can still be maintained by storage of such conditions, states and/or modes in the nonvolatile memory of the controller 102. If power is provided through the power port 30, when "Off," the power supply circuit 156 can still provide limited power to electrical components of the device 12, such as the controller 102 and/or the wireless module 106 for wake-up conditions.

Figure 16:
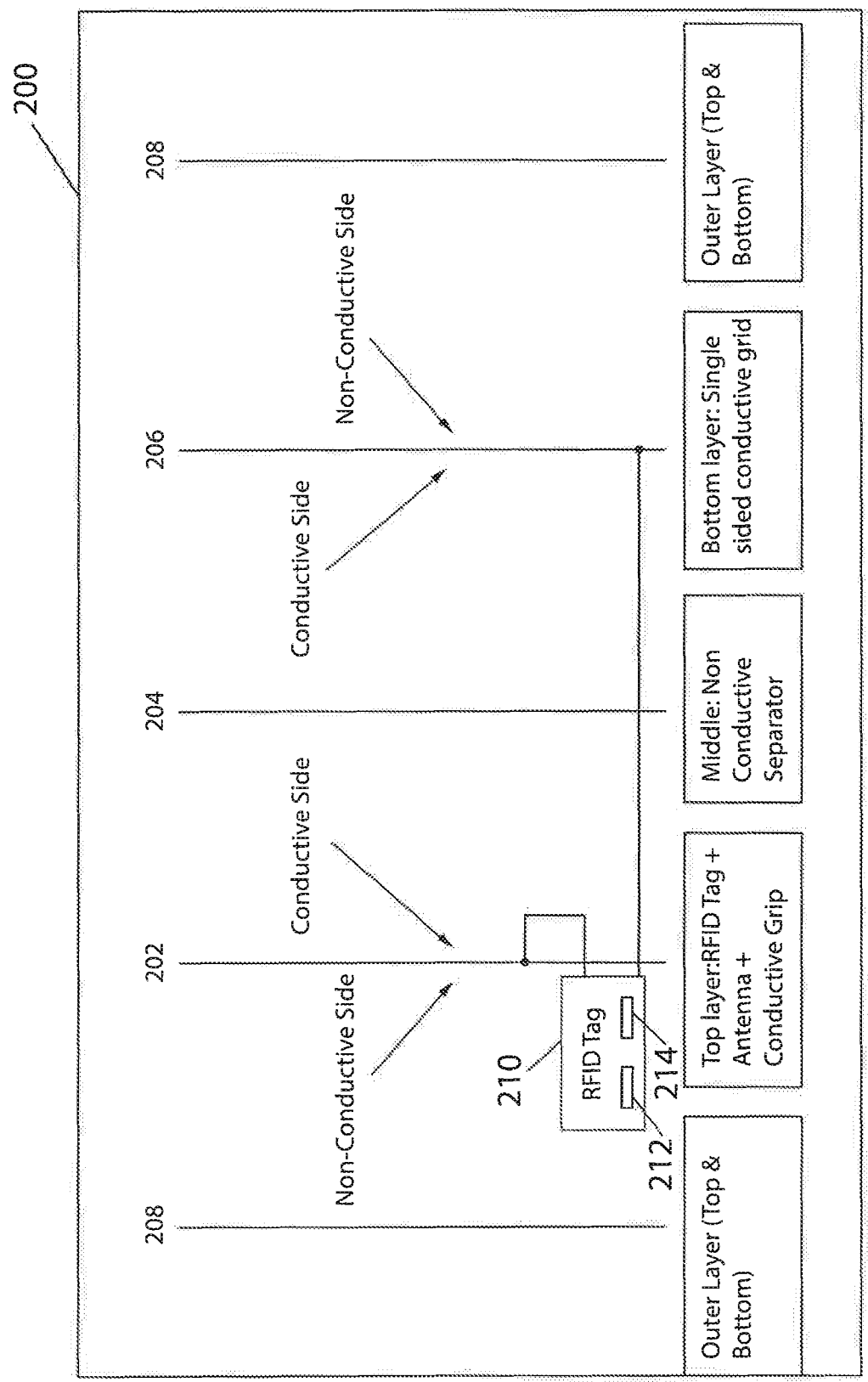
FIG. 16 is a cross sectional view of a battery free wireless sensor pad for use in an electronic fall monitoring system in accordance with an aspect of the invention.

Referring now to FIG. 16, a diagram illustrating a cross sectional view of a battery free wireless sensor pad 200, or simply sensor 200, is provided in accordance with an aspect of the invention. The sensor 200 could be a patient sensor in the system 100 of FIG. 15, such as the wireless patient sensor S3. The sensor 200 may comprise a multilayer pressure sensitive pad formed in top, middle and bottom layers 202, 204 and 206, respectively, enclosed in a cover 20$. The bottom layer 206 may be electrically conductive with a grid made of conductive ink on one side. The other side may be non-conductive and have no ink. The top layer 202 may have an electrically conductive grid made of conductive ink on one side. The other side of the top layer 202 may have an integrated REID tag 210 bonded to the conductive ink thereby forming an antenna. The RFD tag 210 may be connected to the conductive grids of the top layer 202 and the bottom layer 206. The RFID tag 210 may comprise a programmable non-volatile memory 212 and a microprocessor 214. The middle layer 204 may comprise a non-conductive foam layer with a plurality of holes separating the top and bottom layers 202 and 206, respectively.

When pressure is applied on the sensor 200, the conductive grids of the top and bottom layers 202 and 206, respectively, may be in contact, and the resistance between the conductive layers can be measured. As such contact area increases (through the plurality of holes of the middle layer 204), the resistance between the top and bottom layers 202 and 206, respectively, decreases. When there is no pressure on the sensor 200, the conductive grids of the top and bottom layers 202 and 206, respectively, are not in contact and therefore an open circuit occurs. In other words, the conductive grids of the top and bottom layers 202 and 206, respectively, are dual purpose, measuring resistance for sensing, and providing an antenna.

Accordingly, when the device 12 or an RFID reader (not shown) sends an electromagnetic signal to the RFID tag 210 of the sensor 200, the RFID) tag 210 is powered, and the resistance of the top and bottom layers 202 and 206, respectively, is measured and stored in the non-volatile memory 212. The device 12 or RFID reader can send another signal to the RFID tag 210 to read the resistance stored in the non-volatile memory of the RFID tag 210. The device 12 or RFID reader can also identify the type of sensor 200 based on a unique identification (UID) number or pairing key stored in the non-volatile memory 212.

In an alternative aspect, the RFID tag 210 could be replaced with an integrated circuit (IC) Bluetooth and/or NFC device. The Bluetooth and/or NFC device could be powered by over-the-air signals with a Bluetooth or NFC receiver at the device 12 used to receive data from the sensor 200. Accordingly, the sensor 200 could be battery free with Bluetooth or NFC operation.

Figure 17:
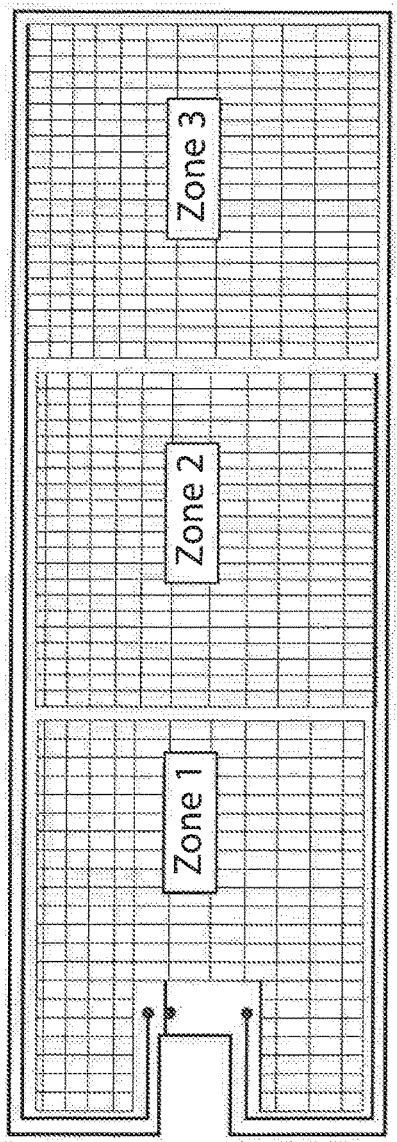
FIG. 17 is a diagram illustrating a sensor of FIG. 16 in accordance with a first aspect of the invention.

Referring now to FIG. 17, a diagram illustrating a multi-zone battery free wireless and/or wired sensor pad 300, or simply sensor 300, implemented consistent with the cross section of the sensor 200 of FIG. 16, is provided in accordance with an aspect of the invention. In the sensor 300, the conductive grids could comprise multiple, electrically separate, zones, such as "Zone 1," "Zone 2" and "Zone 3." Each zone can correspond to a different RFID tag 210, or Bluetooth or NEC device. When pressure is applied to a given zone, the resistance of that zone can be stored in the RFID tag 210, or Bluetooth or NEC device, and can be accessed by a wireless reader such as the device 12. In other words, sensing may be accomplished on a zone by zone basis.

Figure 18:
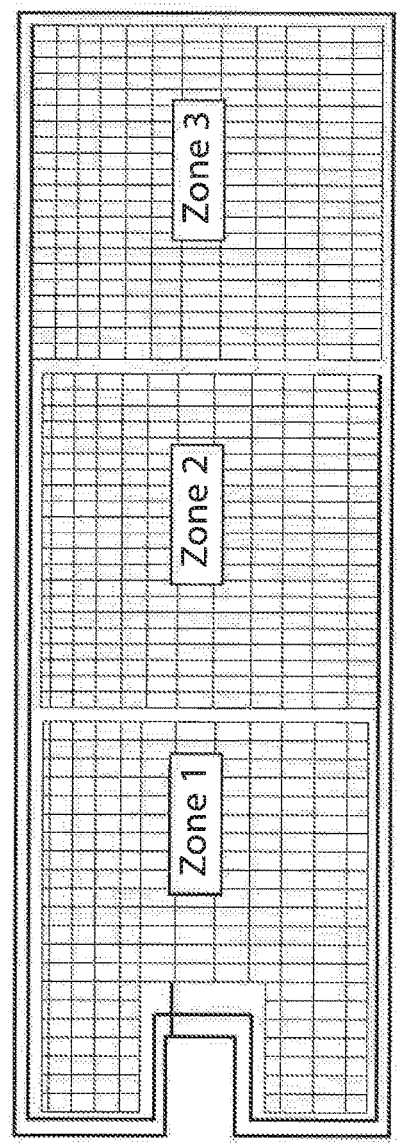
FIG. 18 is a diagram illustrating a sensor of FIG. 16 in accordance with a second aspect of the invention.

Referring now to FIG. 18, a diagram illustrating a multi-zone battery free wireless and/or wired sensor pad 400, or simply sensor 400, implemented consistent with the cross section of the sensor 200 of FIG. 16, is provided in accordance with another aspect of the invention. In the sensor 400, the conductive grids could comprise multiple, electrically separate, zones, such as "Zone 1," "Zone 2" and "Zone 3," with different resistances. Zones can be created with each zone having a different resistance, for example, by changing the tracing of the zone design (trace thickness and/or total area) and/or formulation of the conductive ink. All zones can be connected to a single RFID tag 210, or Bluetooth or NFC device. When pressure is applied to a zone, the resistance of that zone can be stored in the RFID tag 210, or Bluetooth or NEC device, and can be accessed by a wireless reader. Accordingly, the RFID tag 210, or Bluetooth or NFC device, and/or device 12, can determine which zone is active based on the resistance measured.

It should be appreciated that many variations may exist within the scope of the invention. For example, in the sensor 200, the passive RFID or Bluetooth tag can be a separate component that is connected to the top and bottom conductive layers to measure resistance or detect an open or closed circuit. Also, in the sensor 200, the device 12 or other reader can reduce its read range during paring mode with the sensor. Once the sensor is in close proximity or touches (physically contacts) the device 12 or other reader, the UID or pairing key of the sensor can be recorded to complete pairing. The device 12 or other reader can then revert to a standard read range and continue to monitor the paired sensor. Also, in the sensor 200, the device 12 or other reader can utilize an NFC reader. Once the sensor is in close proximity or touches (physically contacts) the device 12 or other reader, NFC pairing is initiated. Once the UID or pairing key of the sensor is recorded, pairing may be complete. The device 12 or other reader can continue to monitor the paired sensors. Also, in one aspect, a battery may be used for Bluetooth Low Energy (BLE) and/or RFID wireless communication initiated via NFC out-of-band pairing.

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left," and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second," and other such numerical terms referring to structures do not imply a sequence or order unless clearly indicated by the context.

When introducing elements or features of the present disclosure and the exemplary embodiments, the articles "a," "an," "the," and "said" are intended to mean that there are one or more of such elements or features. The terms "comprising," "including," and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and elements of different embodiments as coming within the scope of the following claims. All of the publications described herein including patents and non-patent publications are hereby incorporated herein by reference in their entireties.

What is claimed is:

1. An electronic fall monitoring system, comprising: first and second sensor ports, each sensor port being operable toe connect to a patient sensor for detecting an activation indicating a physical presence at the patient sensor and a deactivation indicating a loss of physical presence at the patient sensor; and
    a processor executing a program stored in a non-transient medium, the processor executing the program to:
    select a mode from a plurality of modes, the plurality of modes including a monitor mode in which a sensor port connected to the patient sensor is monitored for the deactivation, an alarm mode in which an alarm is active following the deactivation detected in the monitor mode, and a standby mode in which the alarm is held inactive,
    wherein selection of the monitor mode monitors one of the first and second sensor ports for the deactivation of the patient sensor while monitoring the other of the first and second sensor ports for activation of the patient sensor.

2. The system of claim 1, wherein the first and second sensor ports are virtual connection ports.

3. The system of claim 2, wherein each virtual connection port is configured to connect to the patient sensor through Bluetooth out-of-band pairing via near-field communication (NPC).

4. The system of claim 1, wherein one of the first and second sensor ports is a physical connection port and the other of the first and second sensor ports is virtual connection port.

5. The system of claim 4, further comprising a housing, wherein the physical connection port is configured to connect to a patient through a registered jack (RJ) connector on the housing.

6. The system of claim 1, further comprising a speaker, and further comprising the processor executing to play an audio cue to the speaker.

7. The system of claim 6, further comprising a microphone, and further comprising the processor executing to record a statement from the microphone, determine if the recording is of at least a minimum duration, and only upon determining the recording to be of at least the minimum duration, play the recording to the speaker.

8. The system of claim 6, further comprising a nurse call port, and further comprising the processor executing to play an audio cue to the speaker following connection and disconnection of the nurse call port.

9. The system of claim 1, further comprising a user selectable input, wherein selection of the user selectable input for a shorter duration causes a transition to the standby mode for a shorter amount of time with a first audio cue being played, and wherein selection of the user selectable input for a longer duration causes a transition to the standby mode for a longer amount of time with a second audio cue being played.

10. The system of claim 1, further comprising a user selectable input, wherein selection of the user selectable input during the alarm mode causes an audio cue to be played for resolving the alarm mode.

11. The system of claim 1, wherein each sensor port is operable to connect to a wearable patient sensor, and further comprising the processor executing to receive a rate of patient movement from the wearable patient sensor.

12. An electronic fall monitoring system, comprising:
    first and second indicators;
    a plurality of sensor ports, each sensor port being operable to connect to a patient sensor for detecting an activation indicating a physical presence at the patient sensor and a deactivation indicating a loss of physical presence at the patient sensor; and
    a processor executing a program stored in a non-transient medium, the processor executing the program to:
    select a mode from a plurality of modes, the plurality of modes including a monitor mode in which a sensor port connected to the patient sensor is monitored for the deactivation, an alarm mode in which an alarm is active following the deactivation detected in the monitor mode, and a standby mode in which the alarm is held inactive;
    activate the first indicator to correspond to the mode selected from the plurality of modes; and activate the second indicator to correspond to a power condition.

13. The system of claim 12, further comprising a battery, wherein the power condition comprises a determination of the battery having low charge.

14. The system of claim 13, where the power condition is a first power condition, and further comprising a speaker, and further comprising the processor executing to play an audio cue to correspond to a second power condition.

15. The system of claim 14, wherein the second power condition comprises a determination of the battery having lower charge than in the first power condition.

16. The system of claim 13, further comprising a housing, a power switch on the housing, a power port on the housing for receiving alternating current (AC) power, and a power supply circuit configured to receive power from power port and the battery for distribution to the processor, wherein the power switch completely isolates power from the battery before such power can reach the power supply circuit to prevent battery leakage.

17. The system of claim 12, wherein the first and second indicators are first and second Light Emitting Diodes (LED's), respectively, and wherein the first LED is relatively larger while the second LED is relatively smaller.

18. The system of claim 17, wherein the first LED is a multi-color LED in which a different color is illuminated in each mode of the plurality of modes.

19. An electronic fall monitoring system, comprising:

a plurality of sensor ports, each sensor port being operable to connect to a patient sensor for detecting an activation indicating a physical presence at the patient sensor and a deactivation indicating a loss of physical presence at the patient sensor; and a user selectable input; and a processor executing a program stored in a non-transient medium, the processer executing the program to:

select a mode from a plurality of modes, the plurality of modes including a monitor mode in which a sensor port connected to the patient sensor is monitored for the deactivation, an alarm mode in which an alarm is active following the deactivation detected in the monitor mode, and a standby mode in which the alarm is held inactive, wherein selection of the user selectable input for a shorter duration causes a transition to the standby mode for a shorter amount of time, and wherein selection of the user selectable input for a longer duration causes a transition to the standby mode for a longer amount of time.

20. The system of claim 19, wherein selection of the user selectable input during the alarm mode causes an audio cue to be played for resolving the alarm mode.

* * * * *